(12) United States Patent
Duchon et al.

(10) Patent No.: US 7,959,605 B2
(45) Date of Patent: *Jun. 14, 2011

(54) ANGIOGRAPHIC INJECTOR AND INJECTION METHOD

(75) Inventors: Douglas J. Duchon, Chanhassen, MN (US); Thomas Paulson, Minneapolis, MN (US); Robert F. Wilson, Roseville, MN (US); Jiyan Liu, Maplewood, MN (US)

(73) Assignee: Acist Medical Systems, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/793,498

(22) Filed: Jun. 3, 2010

(65) Prior Publication Data

US 2010/0249587 A1     Sep. 30, 2010

Related U.S. Application Data

(63) Continuation of application No. 10/669,591, filed on Sep. 24, 2003, now Pat. No. 7,753,885, which is a continuation of application No. 09/591,529, filed on Jun. 9, 2000, now Pat. No. 6,656,157, which is a continuation of application No. 08/957,801, filed on Oct. 24, 1997, now Pat. No. 6,221,045, which is a continuation-in-part of application No. 08/946,293, filed on Oct. 7, 1997, now Pat. No. 5,800,397, which is a continuation of application No. 08/426,148, filed on Apr. 20, 1995, now abandoned.

(51) Int. Cl.
*A61M 1/00*     (2006.01)
*A61M 31/00*    (2006.01)
*A61M 37/00*    (2006.01)
*A61B 6/00*     (2006.01)

(52) U.S. Cl. ........... 604/151; 604/67; 604/131; 600/432
(58) Field of Classification Search .................. 604/65, 604/67, 131, 151, 152, 154; 222/52, 56, 222/71; 137/385; 141/18, 21, 95, 153, 192, 141/198; 600/432
See application file for complete search history.

(56) References Cited

U.S. PATENT DOCUMENTS

| | | | |
|---|---|---|---|
| 1,496,126 | A | 3/1874 | Higgins |
| 1,223,243 | A | 4/1917 | Bessesen |
| 3,523,523 | A | 8/1970 | Reich |
| 3,731,679 | A | 5/1973 | Wilhelmson et al. |
| 3,739,943 | A | 6/1973 | Wilhelmson et al. |
| 3,746,038 | A | 7/1973 | Simmons |
| 3,888,239 | A | 6/1975 | Rubinstein |

(Continued)

FOREIGN PATENT DOCUMENTS

EP     0384155     8/1990

(Continued)

*Primary Examiner* — Kevin C Sirmons
*Assistant Examiner* — Catherine N Witczak
(74) *Attorney, Agent, or Firm* — Kramer Levin Naftalis & Frankel LLP

(57) ABSTRACT

An angiographic injector system includes a manifold and valve which selectively connects either a syringe pump or a low pressure system to a catheter which is inserted into a patient. The valve is normally biased to a state which connects the low pressure system to the catheter for pressure monitoring, saline flushing, or aspirating functions. When an injection is to be made, the valve automatically switches so that the low pressure system is disconnected and not exposed to high pressure, while the syringe pump is connected through the manifold to the catheter.

11 Claims, 31 Drawing Sheets

U.S. PATENT DOCUMENTS

| | | |
|---|---|---|
| 3,940,224 A | 2/1976 | Armour |
| 4,065,230 A | 12/1977 | Gezan |
| 4,261,359 A | 4/1981 | Chein |
| 4,471,775 A | 9/1984 | Clair et al. |
| 4,502,488 A | 3/1985 | Degironimo et al. |
| 4,512,764 A | 4/1985 | Wunsch |
| 4,535,820 A | 8/1985 | Raines |
| 4,559,036 A | 12/1985 | Wunsch |
| 4,596,575 A | 6/1986 | Rosenberg et al. |
| 4,604,093 A | 8/1986 | Brown et al. |
| 4,624,661 A | 11/1986 | Arimond |
| 4,670,006 A | 6/1987 | Sinnett et al. |
| 4,684,365 A | 8/1987 | Reinicke |
| 4,837,857 A | 6/1989 | Scheller et al. |
| 4,854,324 A | 8/1989 | Hirschman et al. |
| 4,908,017 A | 3/1990 | Howson et al. |
| 4,919,167 A | 4/1990 | Manska |
| 4,966,199 A | 10/1990 | Ruschke |
| 4,966,579 A | 10/1990 | Polaschegg |
| 5,012,845 A | 5/1991 | Averette |
| 5,226,886 A | 7/1993 | Skakoon et al. |
| 5,249,579 A | 10/1993 | Hobbs et al. |
| 5,254,101 A | 10/1993 | Trombley, III |
| 5,267,964 A | 12/1993 | Karg |
| 5,346,470 A | 9/1994 | Hobbs et al. |
| 5,494,036 A | 2/1996 | Uber, III et al. |
| 5,515,851 A | 5/1996 | Goldstein |
| 5,554,119 A | 9/1996 | Harrison et al. |
| 5,556,001 A | 9/1996 | Weissman et al. |
| 5,569,181 A | 10/1996 | Heilman et al. |
| 5,575,770 A | 11/1996 | Melsky et al. |
| 5,665,074 A | 9/1997 | Kelly |
| 5,672,155 A | 9/1997 | Riley et al. |
| 5,739,508 A | 4/1998 | Uber, III |
| 5,743,872 A | 4/1998 | Kelly |
| 5,779,666 A | 7/1998 | Teirstein |
| 5,795,333 A | 8/1998 | Reilly et al. |
| 5,806,519 A | 9/1998 | Evans, III et al. |
| 5,807,340 A | 9/1998 | Pokras |
| 5,808,203 A | 9/1998 | Nolan, Jr. et al. |
| 5,840,026 A | 11/1998 | Uber, III |
| 5,843,037 A | 12/1998 | Uber, III |
| 5,868,728 A | 2/1999 | Giungo et al. |
| 5,873,861 A | 2/1999 | Hitchins et al. |
| 5,885,216 A | 3/1999 | Evans, III et al. |
| 5,911,708 A | 6/1999 | Teirstein |
| 5,920,054 A | 7/1999 | Uber, III |
| 5,925,022 A | 7/1999 | Battiato et al. |
| 5,947,935 A | 9/1999 | Rhinechart et al. |
| 5,968,014 A | 10/1999 | Neftel et al. |
| 6,030,359 A | 2/2000 | Nowosielski |
| RE36,648 E | 4/2000 | Uber, III et al. |
| 6,050,450 A | 4/2000 | Gardos |
| 6,096,011 A | 8/2000 | Trombley, III et al. |
| 6,149,627 A | 11/2000 | Uber, III |
| 6,197,000 B1 | 3/2001 | Reilly et al. |
| 6,306,117 B1 | 10/2001 | Uber, III |
| 6,317,623 B1 | 11/2001 | Griffiths et al. |
| 6,339,718 B1 | 1/2002 | Zatezalo et al. |
| RE37,602 E | 3/2002 | Uber, III et al. |
| 6,385,483 B1 | 5/2002 | Uber, III et al. |
| 6,397,098 B1 | 5/2002 | Uber, III et al. |
| 6,402,717 B1 | 6/2002 | Reilly et al. |
| 6,440,107 B1 | 8/2002 | Trombley, III et al. |
| 6,442,418 B1 | 8/2002 | Evans, III et al. |
| 6,471,674 B1 | 10/2002 | Emig et al. |
| 6,475,192 B1 | 11/2002 | Reilly et al. |
| 6,520,930 B2 | 2/2003 | Critchlow et al. |
| 6,539,248 B1 | 3/2003 | Moroski |
| 6,643,537 B1 | 11/2003 | Zatezalo et al. |
| 6,652,489 B2 | 11/2003 | Trocki et al. |
| 6,673,033 B1 | 1/2004 | Sciulli et al. |
| 6,699,219 B2 | 3/2004 | Emig et al. |
| 6,731,971 B2 | 5/2004 | Evans, III et al. |
| 6,733,477 B2 | 5/2004 | Cowan et al. |
| 6,733,478 B2 | 5/2004 | Reilly et al. |
| 6,743,202 B2 | 6/2004 | Hirschman et al. |
| 6,889,074 B2 | 5/2005 | Uber, III et al. |
| 6,901,283 B2 | 5/2005 | Evans, III et al. |
| 6,939,302 B2 | 9/2005 | Griffiths et al. |
| 7,753,885 B2 * | 7/2010 | Duchon et al. ................ 604/151 |
| 2001/0018937 A1 | 9/2001 | Nemoto |
| 2002/0107501 A1 | 8/2002 | Smith et al. |
| 2005/0107697 A1 | 5/2005 | Berke |

FOREIGN PATENT DOCUMENTS

| | | |
|---|---|---|
| WO | WO 96/20745 | 7/1996 |

\* cited by examiner

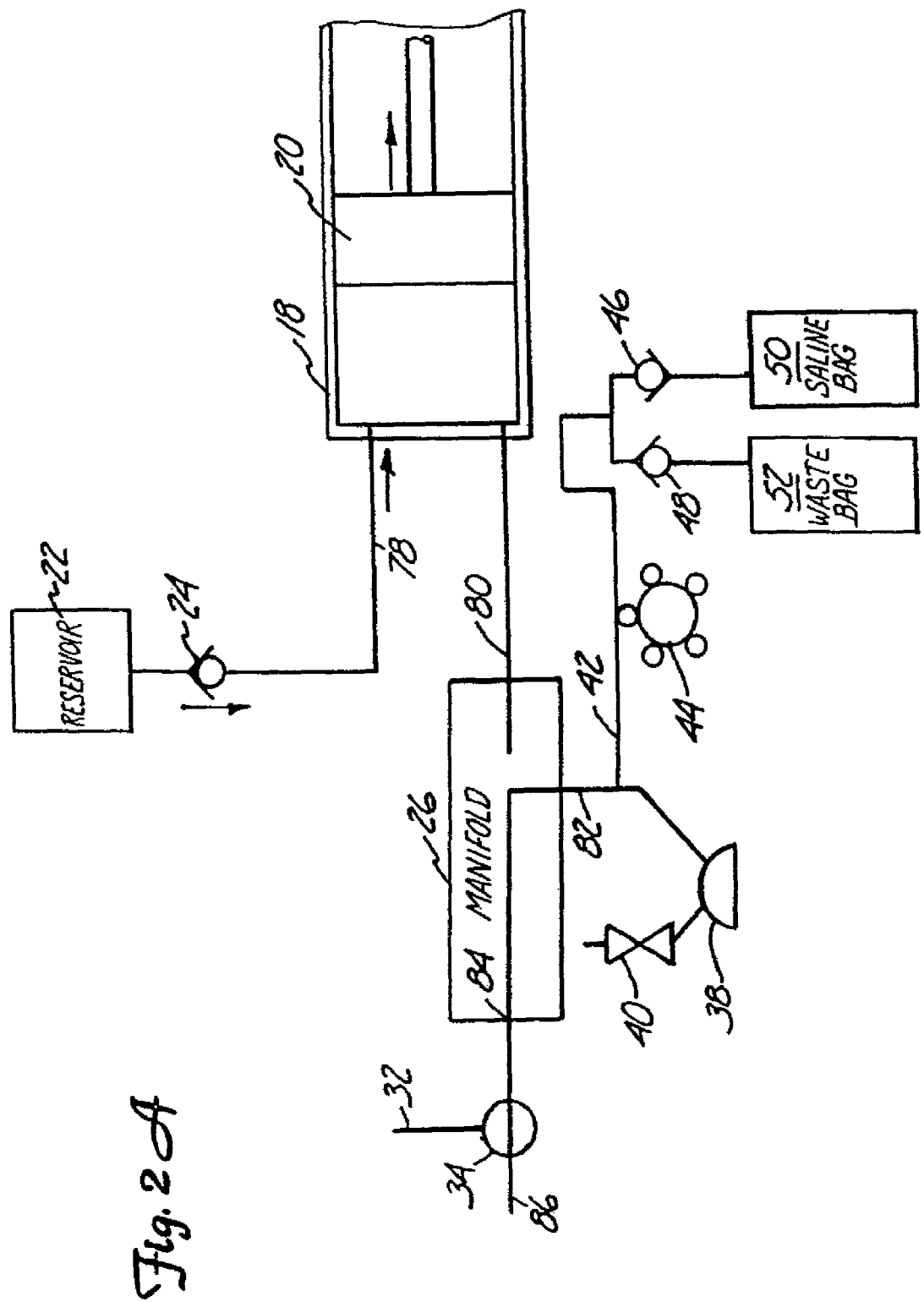

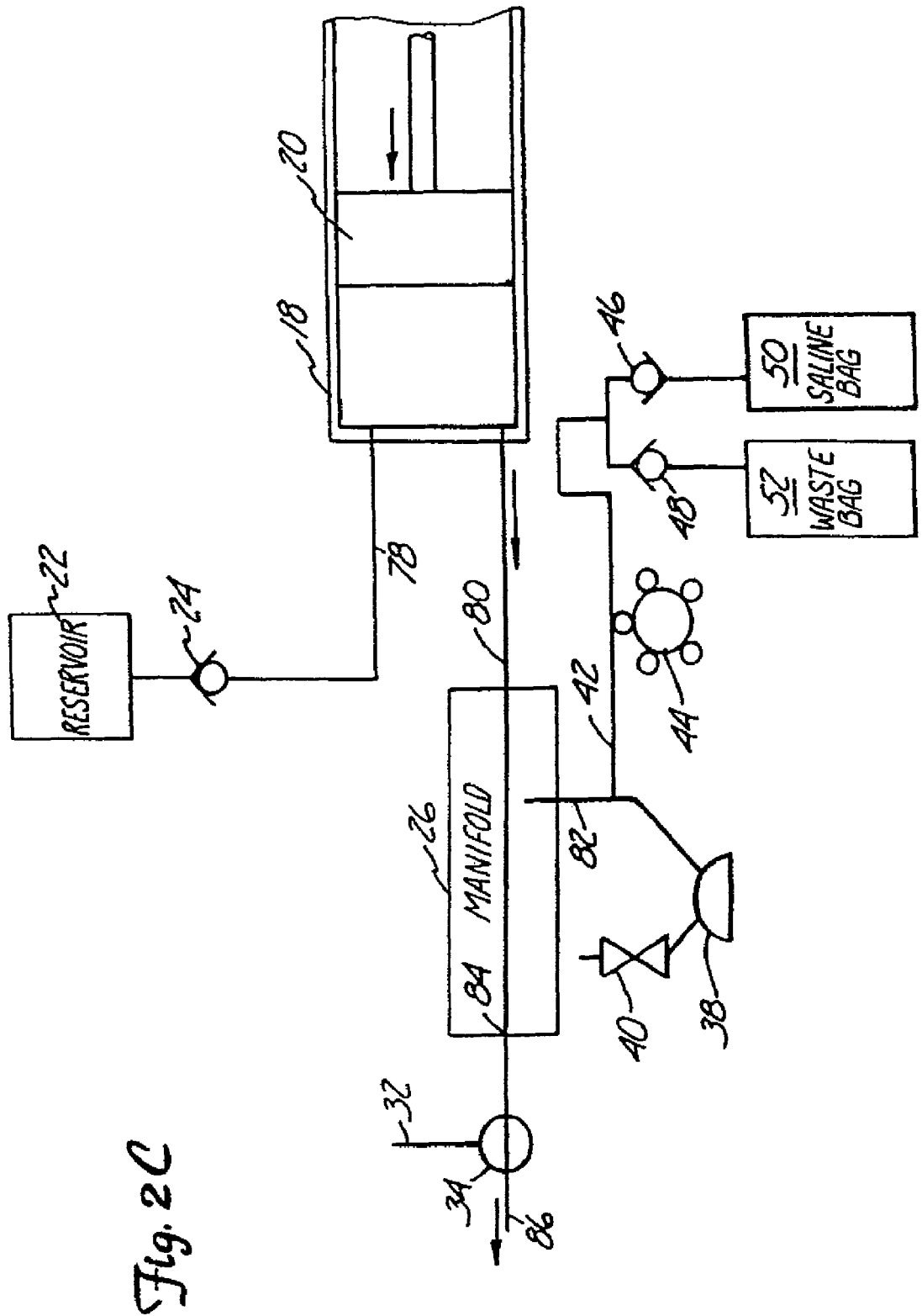

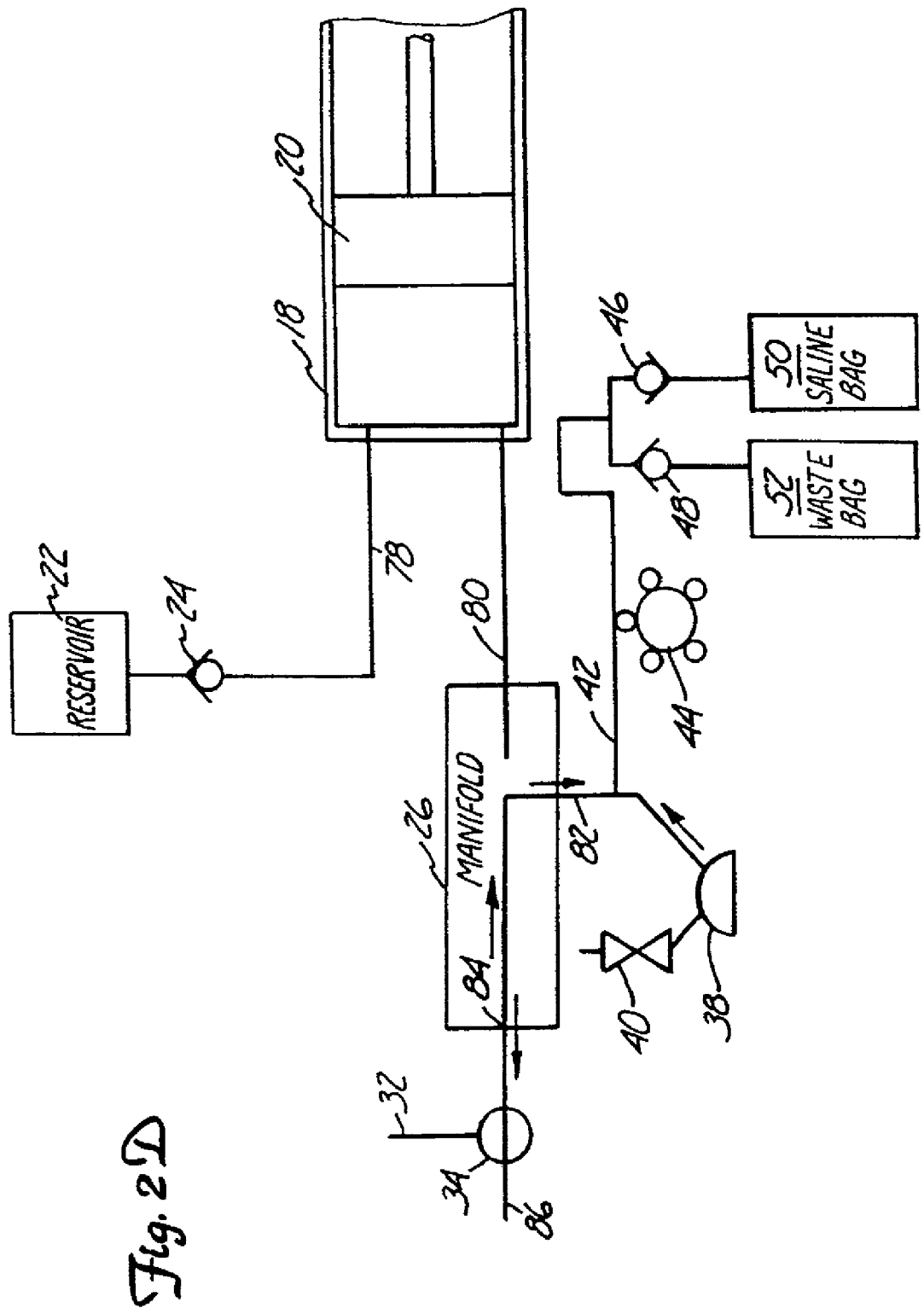

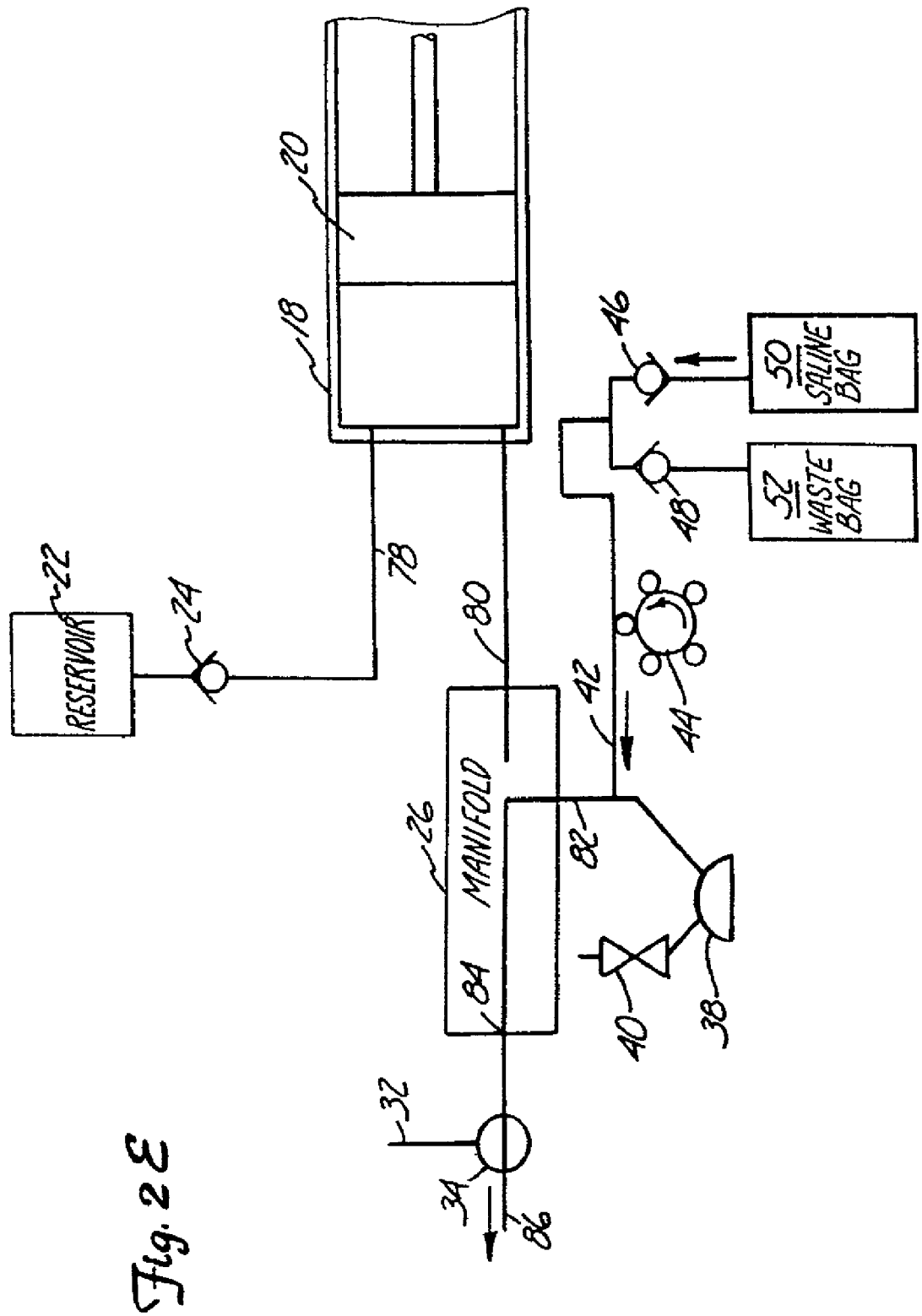

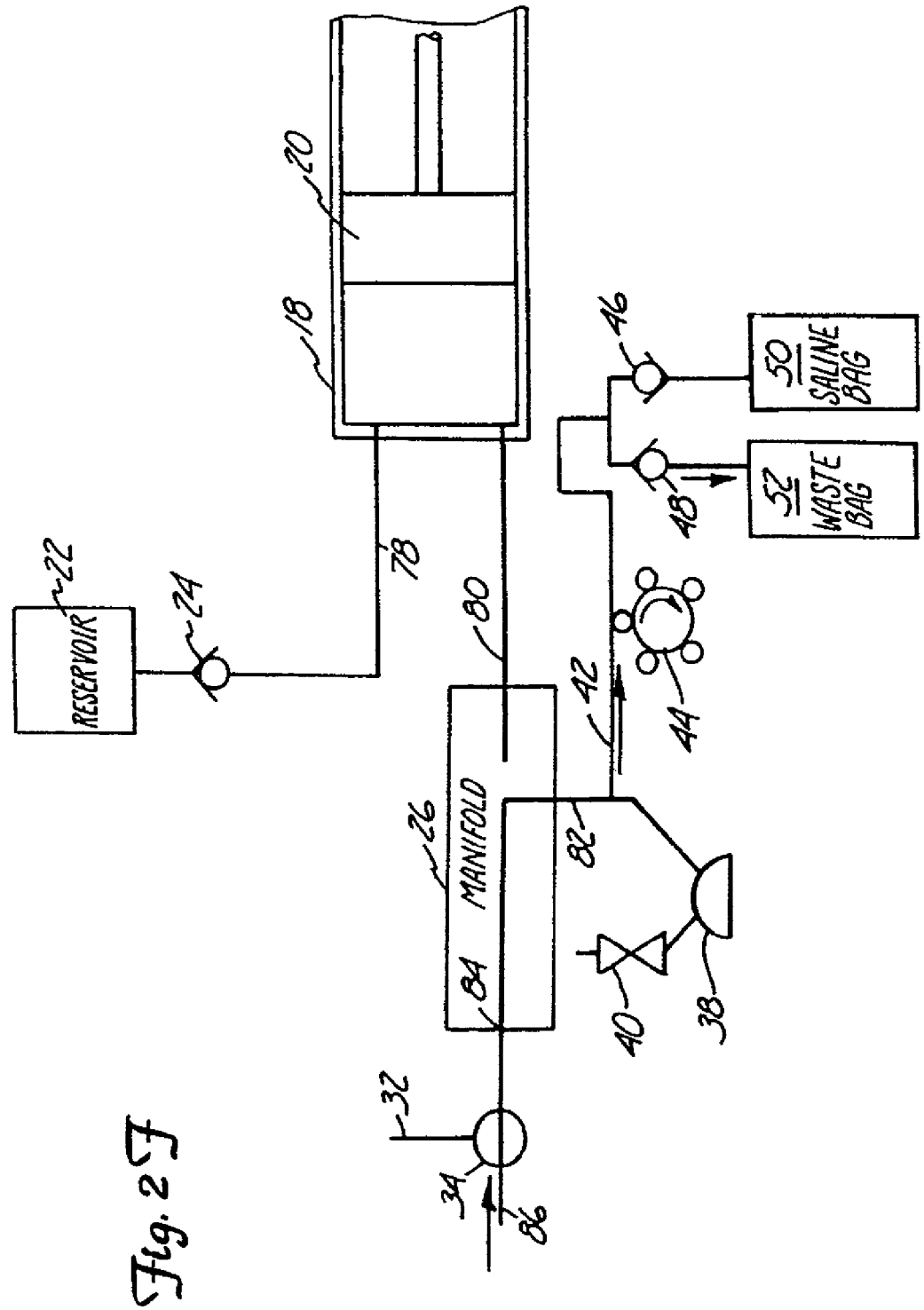

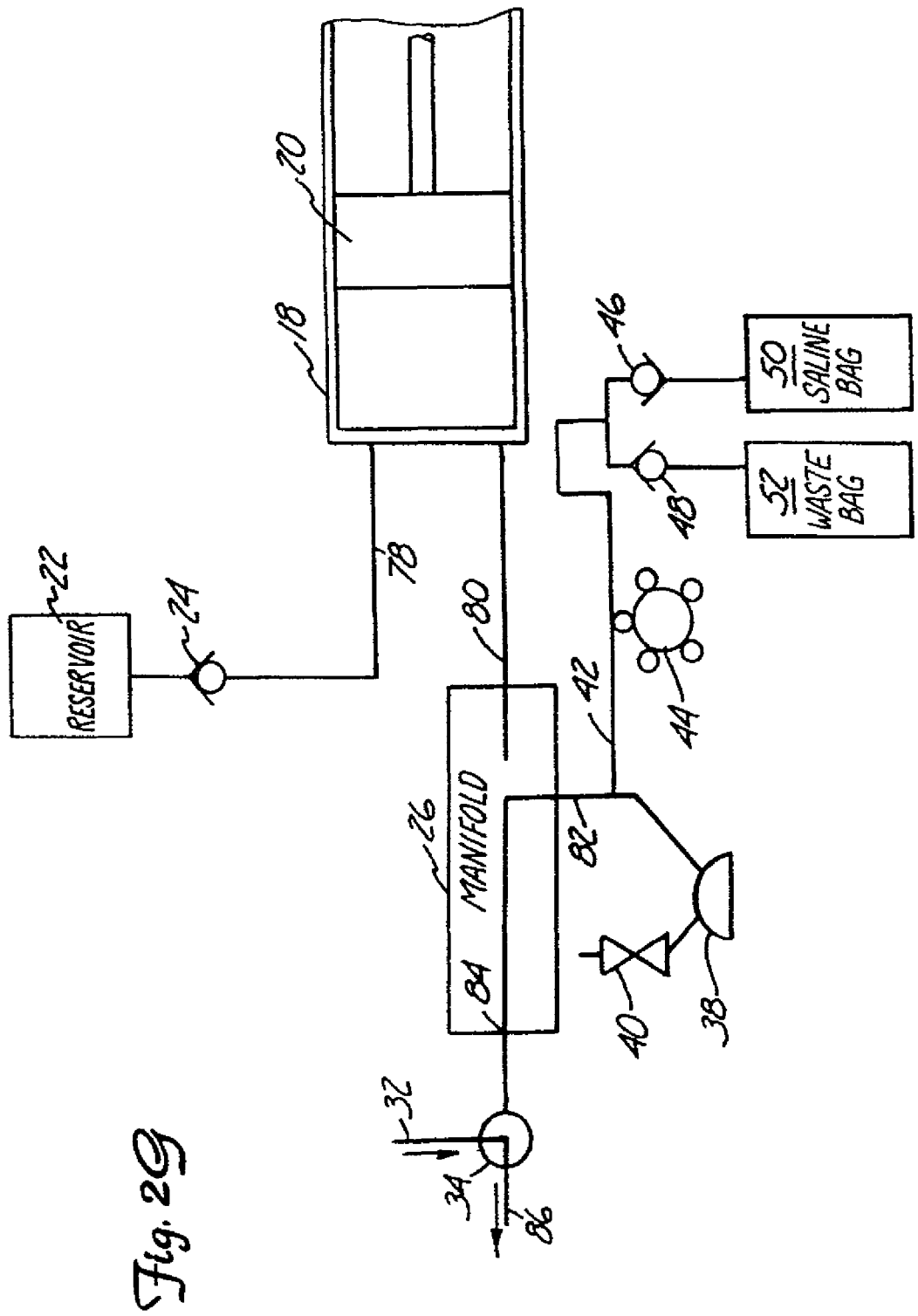

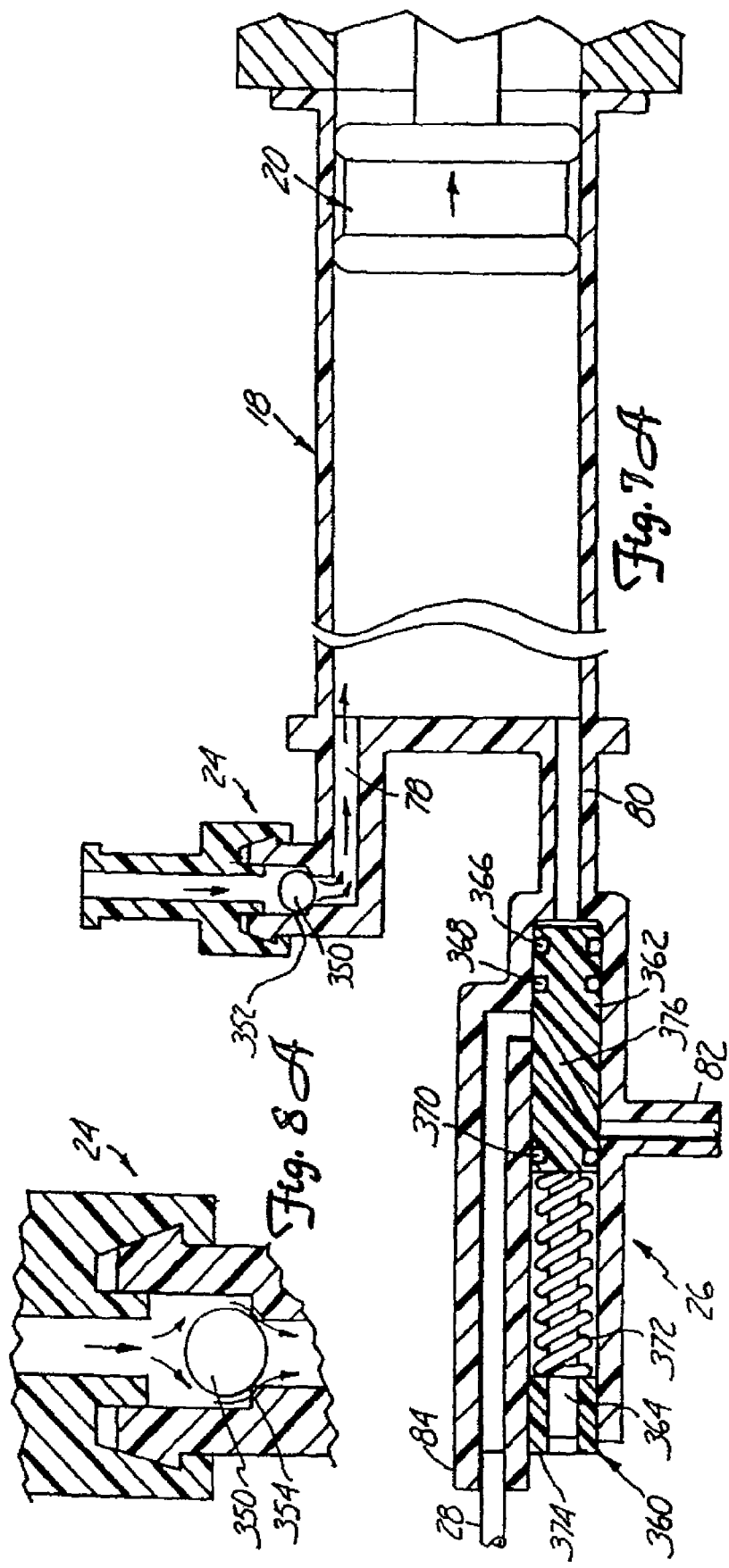

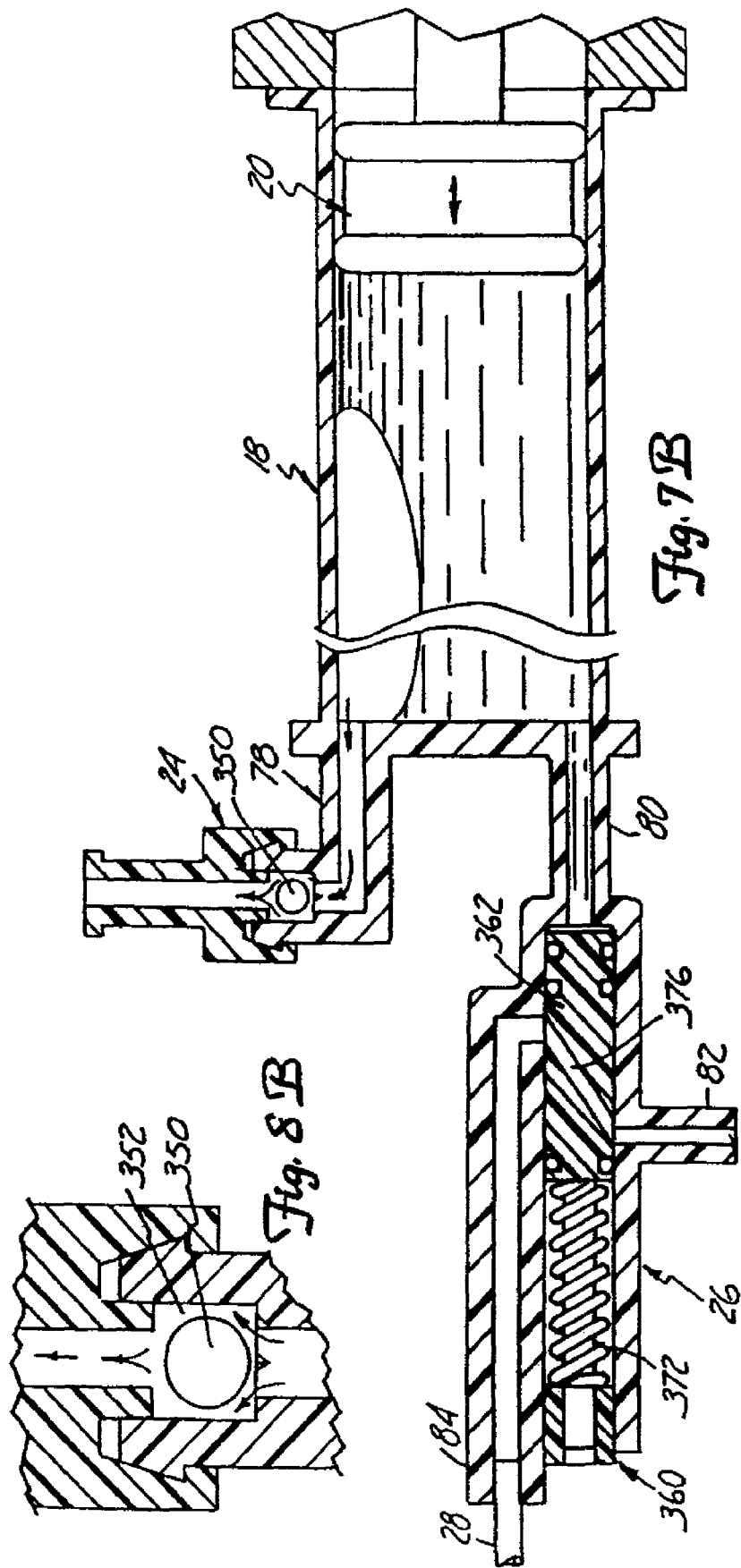

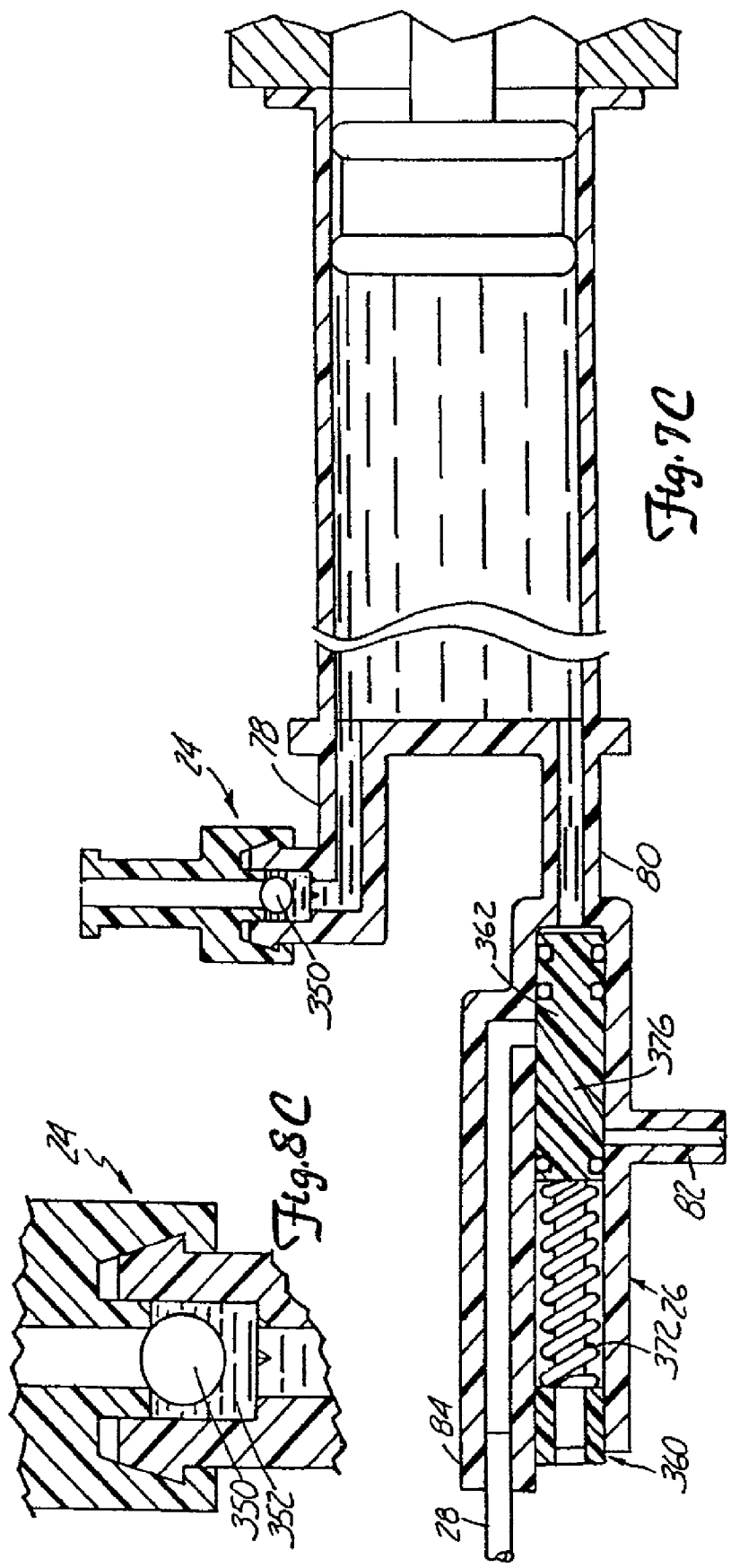

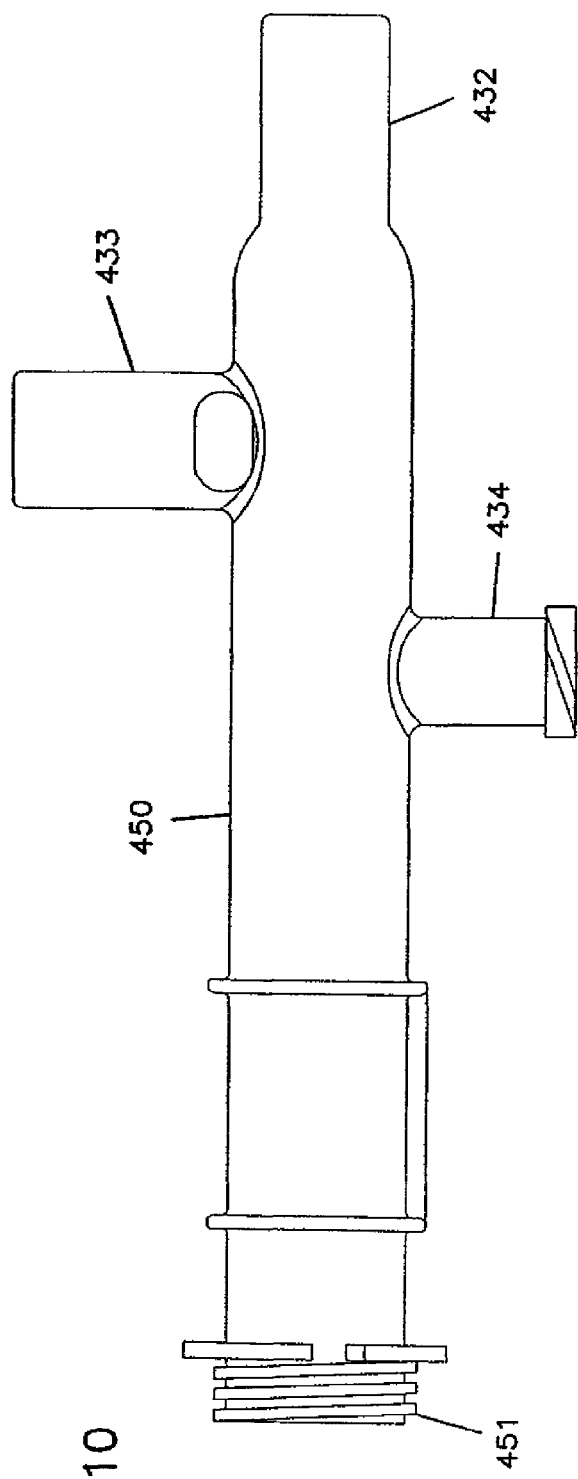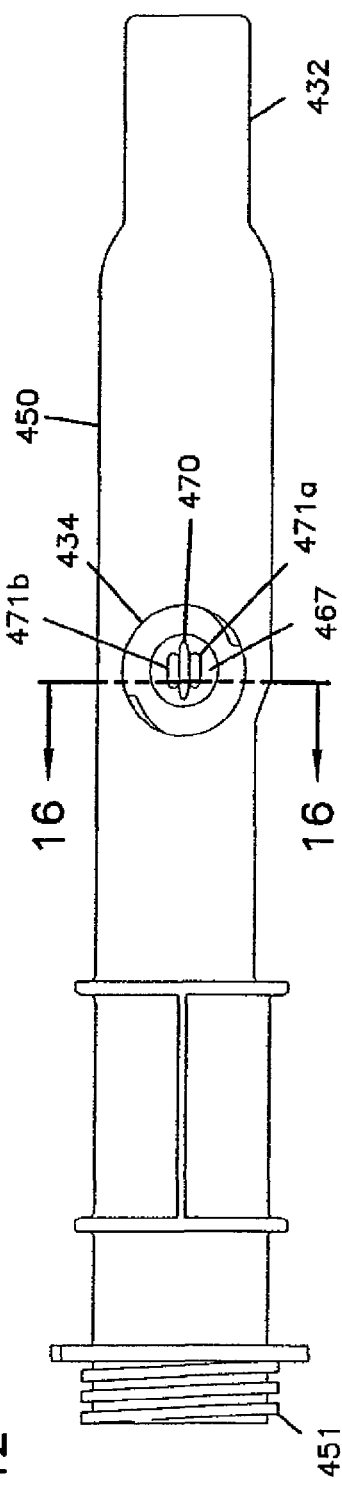
FIG. 10
FIG. 12

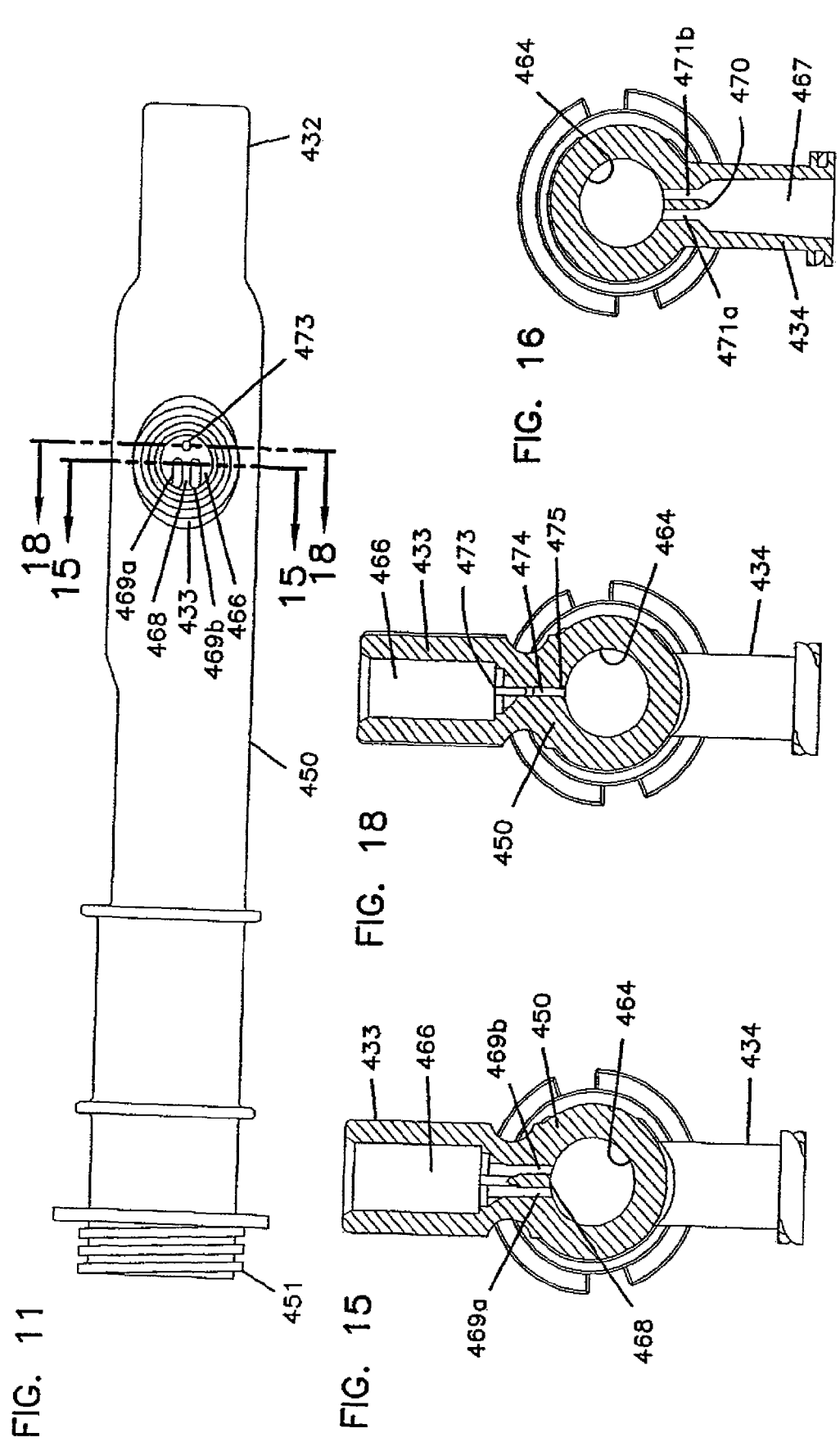

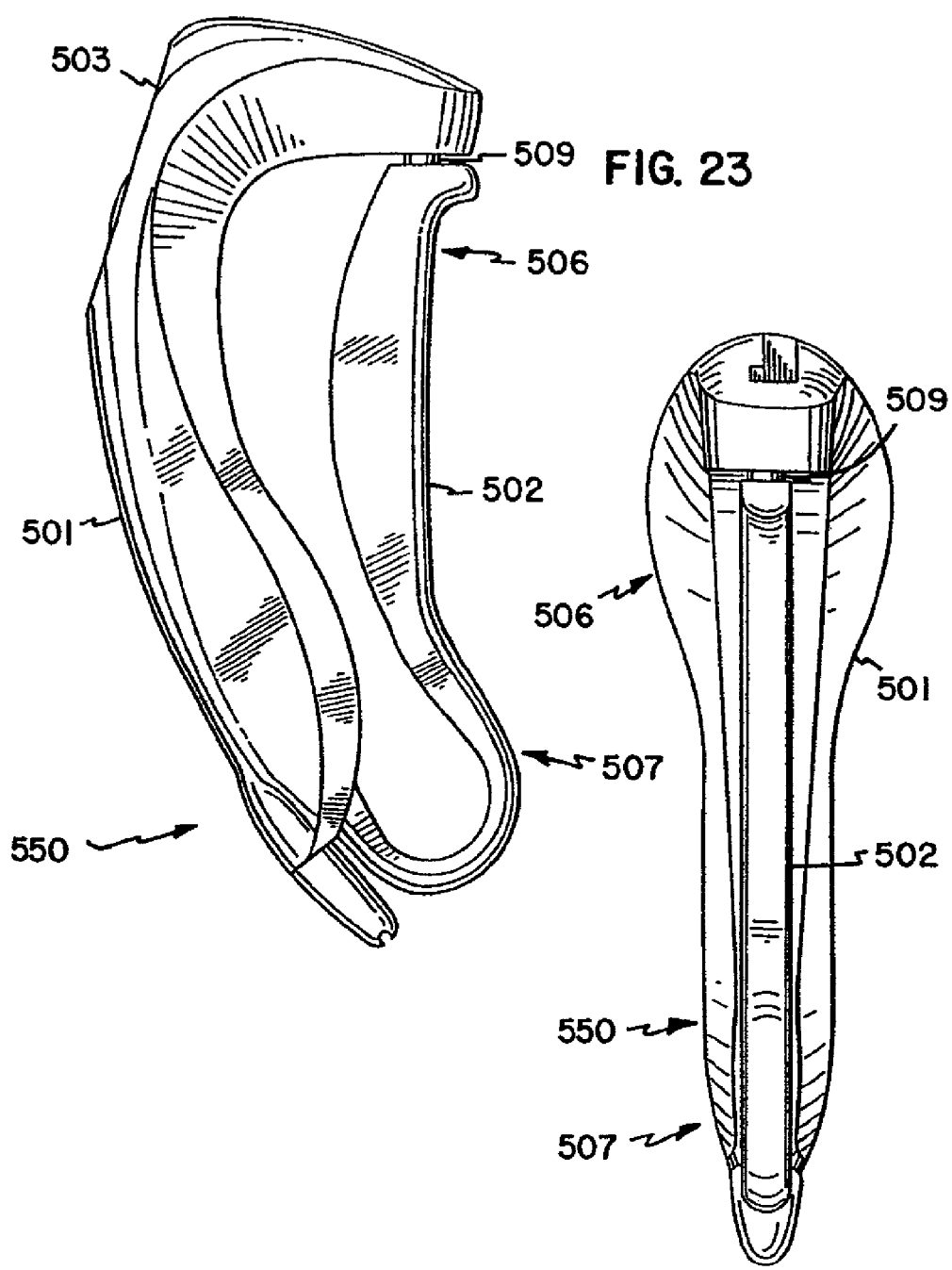

FIG. 24
FIG. 25
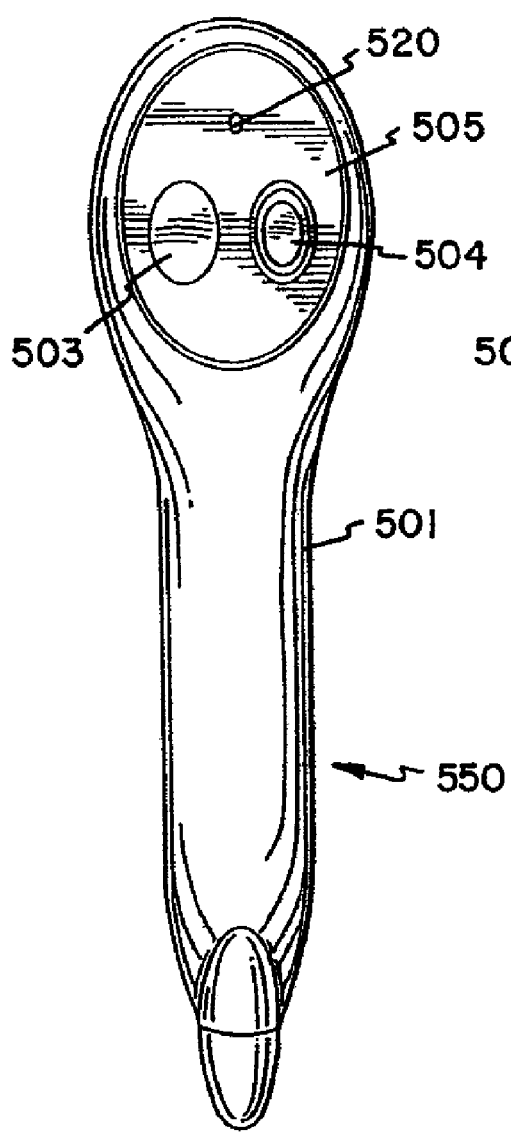
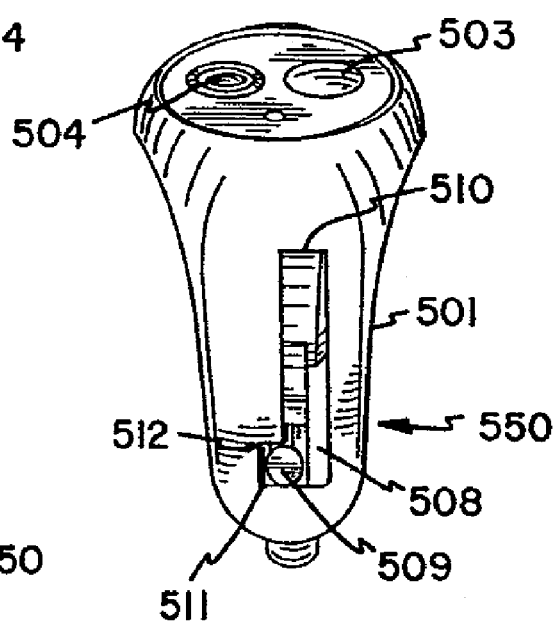

ANGIOGRAPHIC INJECTOR AND INJECTION METHOD

RELATED APPLICATIONS

This application is a continuation of U.S. Ser. No. 10/669,591, filed Sep. 24, 2003 which is a continuation of U.S. Ser. No. 09/591,529, filed Jun. 9, 2000, now U.S. Pat. No. 6,656,157 which is a continuation of U.S. Ser. No. 08/957,801, filed Oct. 24, 1997, now U.S. Pat. No. 6,221,045, which is a continuation-in-part of U.S. Ser. No. 08/946,293, filed Oct. 7, 1997, now U.S. Pat. No. 5,800,397, which is a file wrapper continuation application of U.S. Ser. No. 08/426,148, filed Apr. 20, 1995, now abandoned, which applications are hereby incorporated by reference.

FIELD OF THE INVENTION

This invention relates to angiography and more specifically, the injector system used to inject a medical fluid such as radiographic contrast material into living organisms.

BACKGROUND OF THE INVENTION

One of the major systems in the human body is the circulatory system. Components of the circulatory system include the heart, blood vessels, and blood, all of which are vital for the transportation of materials between the external environment and the cells and tissues of the body.

The blood vessels are the network of passageways through which blood travels in a human or animal body. Specifically, the arteries carry oxygenated blood away from the left ventricle of the heart. The arteries are arranged in progressively decreasing diameter and pressure capability from the aorta, which carries the blood immediately out of the heart to other major arteries, to smaller arteries, to arterioles, and finally to capillaries, where exchange of nutrients and waste products between the blood and the cells and tissues of the body occur. Generally, veins carry oxygen depleted blood back to the right atrium of the heart using a progressively increasing diameter network of venules and veins.

Angiography is a procedure used in the diagnosis and treatment of cardiovascular conditions including abnormalities or restrictions in blood vessels. During angiography, a radiographic image of the heart or a vascular structure is obtained by injecting a radiographic contrast material through a catheter into a vein or artery. The injected contrast material can pass to vascular structures in fluid communication with the vein or artery in which the injection is made. X-rays are passed through the region of the body in which the contrast material was injected. The X-rays are absorbed by the contrast material, causing a radiographic outline or image of the blood vessel containing the contrast material. The x-ray images of the blood vessels filled with contrast material are usually recorded onto film or videotape and are displayed on a fluoroscope monitor.

Angiography provides an image of the cardiac or vascular structures in question. This image may be used solely for diagnostic purposes, or the image may be used during a procedure such as angioplasty where a balloon is inserted into the vascular system and inflated to open a stenosis caused by atherosclerotic plaque buildup.

Currently, during angiography, after a catheter is placed into a vein or artery (by direct insertion into the vessel or through a skin puncture site), the angiographic catheter is connected to either a manual or an automatic contrast injection mechanism.

A simple manual contrast injection system typically has a syringe and a catheter connection. The syringe includes a chamber with a plunger therein. Radiographic contrast material is suctioned into the chamber. Any air is removed by actuating the plunger while the catheter connection is facing upward so that any air, which floats on the radiographic contrast material, is ejected from the chamber. The catheter connection is then attached to a catheter that is positioned in a vein or artery in the patient.

The plunger is manually actuated to eject the radiographic contrast material from the chamber, through the catheter, and into a vein or artery. The user of the manual contrast injection system may adjust the rate and volume of injection by altering the manual actuation force applied to the plunger.

Often, more than one type of fluid injection is desired, such as a saline flush followed by the radiographic contrast material. One of the most common manual injection mechanisms used today includes a valve mechanism which controls which of the fluids will flow into the valuing mechanism and out to the catheter within the patient. The valve mechanism can contain a plurality of manual valves that the user manually opens and closes to direct fluid flow to a particular fluid channel. When the user aspirates or injects contrast fluid into or out of the chamber, the fluid flows through the path of least resistance directed by the position of the valves. By changing the valve positions, one or more other fluids may be injected.

Manual injection systems are typically hand actuated. This allows user control over the quantity and pressure of the injection. However, generally, most manual systems can only inject the radiographic contrast material at maximum pressure that can be applied by the human hand (i.e., 150 p.s.i.). Also, the quantity of radiographic contrast material is typically limited to a maximum of about 12 cc. Moreover, there are no safety limits on these manual contrast injection systems which restrict or stop injections that are outside of predetermined parameters (such as rate or pressure) and there are no active sensors to detect air bubbles or other hazards.

Currently used motorized injection devices consist of a syringe connected to a linear actuator. The linear actuator is connected to a motor, which is controlled electronically. The operator enters into the electronic control a fixed volume of contrast material to be injected at a fixed rate of injection. Typically, the fixed rate of injection consists of a specified initial rate of flow increase and a final rate of injection until the entire volume of contrast material is injected. There is no interactive control between the operator and machine, except to start or stop the injection. Any change in flow rate must occur by stopping the machine and resetting the parameters.

The lack of ability to vary the rate of injection during injection can result in suboptimal quality of angiographic studies. This is because the optimal flow rate of injections can vary considerably between patients. In the cardiovascular system, the rate and volume of contrast injection is dependent on the volume and flow rate within the chamber or blood vessel being injected. In many or most cases, these parameters are not known precisely. Moreover, the optimal rate of injection can change rapidly, as the patient's condition changes in response to drugs, illness, or normal physiology. Consequently, the initial injection of contrast material may be insufficient in volume or flow rate to outline a desired structure on an x-ray image, necessitating another injection. Conversely, an excessive flow rate might injure the chamber or blood vessel being injected, cause the catheter to be displaced (from the jet of contrast material exiting the catheter tip), or lead to toxic effects from contrast overdose (such as abnormal heart rhythm).

At present, the operator can choose between two systems for injecting contrast material: a manual injection system which allows for a variable, operator interactive flow rate of limited flow rate and a preprogrammed motorized system without operator interactive feedback (other than the operator can start/stop the procedure). Accordingly, there is a need for improvement in the equipment and procedures used for performing diagnostic imaging studies.

SUMMARY OF THE INVENTION

The present invention is an angiographic injection system which includes both high pressure and low pressure systems. The high pressure system includes a motor driven injector pump which supplies radiographic contrast material under high pressure to a catheter. The low pressure system includes, for example, a pressure transducer for measuring blood pressure and a pump which is used to both for delivering saline solution to the patient and for aspirating waste fluid. In the present invention, a manifold is connected to the syringe pump, the low pressure system, the catheter which is inserted into the patient. A valve associated with the manifold is normally maintained in a first state which connects the low pressure system to the catheter through the manifold. When pressure from the syringe pump reaches a predetermined level, the valve switches to a second state which connects the syringe pump to the catheter, while disconnecting the low pressure system from the catheter.

It will be appreciated that while the invention is described with reference to an angiographic injector, the devices and methods disclosed herein are applicable for use in performing other diagnostic and interventional procedures.

BRIEF DESCRIPTION OF THE DRAWINGS

FIGS. 2A-2G are diagrams illustrating operations of the system of FIG. 1.

FIGS. 7A-7D illustrate the operation of the inlet check valve and manifold during contrast fill, air purge, and patient inject operations.

FIGS. 8A-8C illustrate operation of the inlet check valve in greater detail.

FIG. 10 is a side view of one embodiment of the shell of a manifold according to the invention.

FIG. 11 is a top view of the embodiment of the manifold shell of FIG. 10.

FIG. 12 is a bottom view of the embodiment of the manifold shell of FIGS. 10 and 11.

FIG. 15 is a transverse cross section view through line 15-15 of FIG. 11.

FIG. 16 is a transverse cross section view through line 16-16 of FIG. 12.

FIG. 18 is a cross section view through line 18-18 of FIG. 11.

FIG. 22 is a side view of the embodiment of a remote control of FIG. 21.

FIG. 23 is a front view of the embodiment of a remote control of FIG. 21.

FIG. 24 is a rear view of the embodiment of a remote control of FIG. 21.

FIG. 25 is a top view of the embodiment of a remote control of FIG. 21.

DETAILED DESCRIPTION OF THE PREFERRED EMBODIMENTS

A. Application Ser. No. 08/426,149

Figure 1:
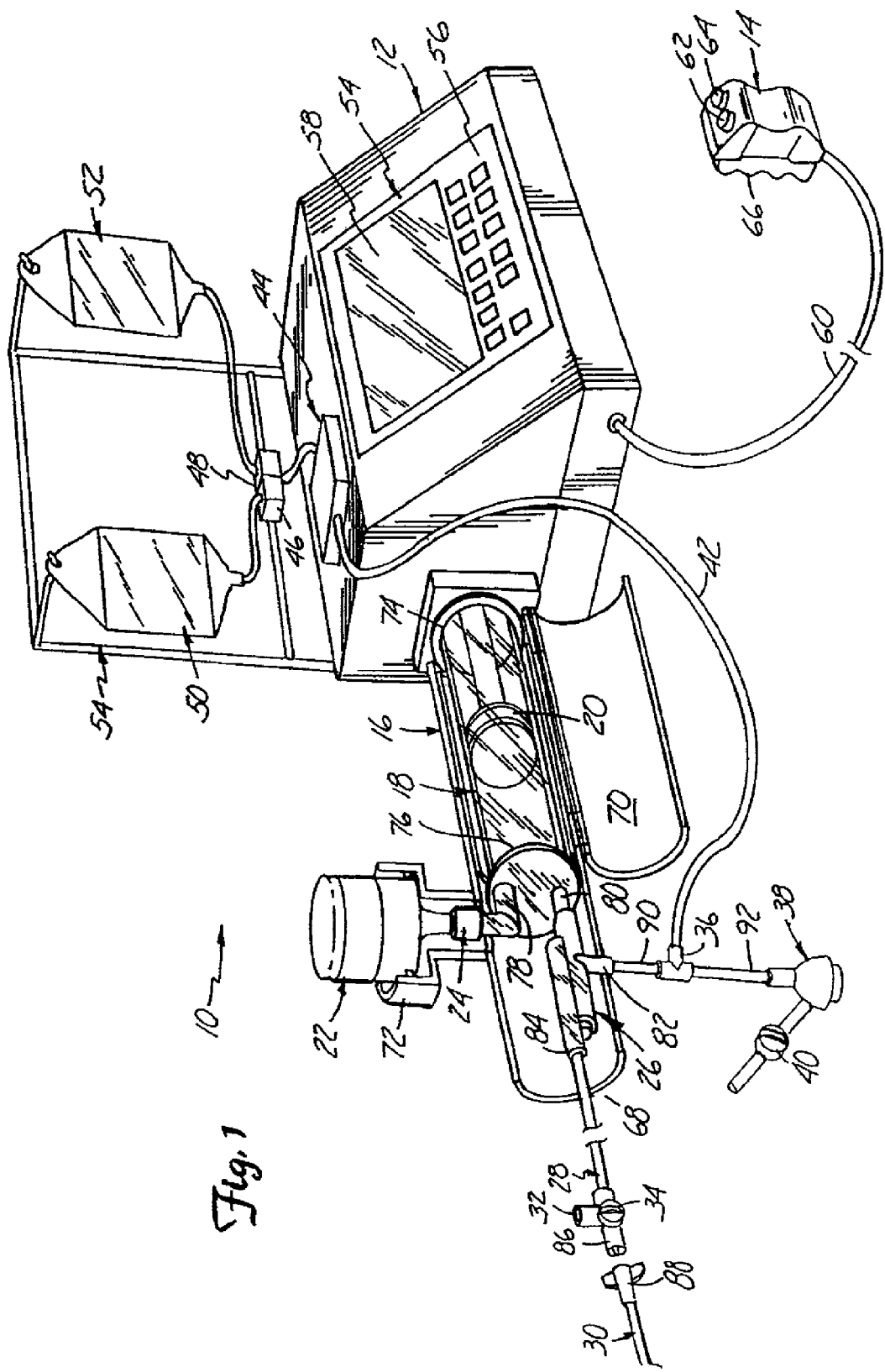
FIG. 1 is a perspective view illustrating a preferred embodiment of the angiographic injector system of the present invention.

FIG. 1 shows angiographic injector system 10 for injecting radiographic contrast material into a blood vessel under interactive physician control. System 10 includes main console 12, hand held remote control 14, syringe holder 16, syringe body 18, syringe plunger 20, radiographic material reservoir (bottle) 22, one-way valve 24, manifold 26, high pressure tube 28, catheter 30, patient medication port 32, three-way stop-cock 34, T-connector 36, pressure transducer 38, stop-cock 40, tubing 42, peristaltic pump 44, saline check valve 46, waste check valve 48, saline bag 50, waste bag 52, and bag support rack 54.

Console 12 houses the electrical controls for system 10, together with the motors which drive piston 20 and peristaltic pump 44. On the front surface of console 12, user interface 54 provides control switches 56 and display 58 through which the user may enter control settings and monitor the operational state of system 10.

Remote control 14 is connected to console 12 by cable 60 (although in other embodiments remote control 14 may be connected by a wireless connection such as an RF, infrared optic, or ultrasonic link). Remote control 14 is, in the embodiment shown in FIG. 1, a hand-held control which includes reset and saline push button switches 62 and 64, respectively, and flow rate control lever or trigger 66. By squeezing trigger 66, the user can provide a command signal to console 12 to provide a continuously variable injection rate.

Syringe holder 16 projects from the left hand side of console 12. Syringe holder 16 is preferably a clear material, and includes a half cylindrical back shell 68, a half cylindrical front door 70 (which is shown in open position in FIG. 1), and reservoir holder 72.

Syringe 18 is a transparent or translucent plastic cylinder having its open end 74 connected to console 12. Closed end 76 of syringe 18 contains two ports: upper port 78 and lower port 80.

Plunger 20 is movable within syringe body 18. Plunger 20 is connected to, and driven by a motor located within console 12.

Radiographic contrast material reservoir 22 is connected through one-way check valve 24 to upper port 78. Radiographic contrast material is drawn from reservoir 22 through check valve 24 and upper port 78 into the pumping chamber defined by syringe body 18 and plunger 20. Check valve 24 is preferably a weighted one-way valve which permits air to flow from syringe body 18 back into reservoir 22, but will not permit radiographic contrast material to flow from syringe body 18 to reservoir 22. This permits automatic purging of air from the system, as will be described in more detail later.

Lower port 80 of syringe body 18 is connected to manifold 26. Manifold 26 includes a spring biased spool valve which normally connects transducer/saline port 82 and patient port 84. When radiographic contrast material is to be injected, the pressure of the radiographic material causes the spool valve to change states so that lower port 80 is connected to patient port 84.

High pressure tube 28 is a flexible tube which connects patient port 84 to catheter 30. Three-way stop-cock 34 is located at the distal end of tube 28. Rotatable luer lock connector 86 is connected to stop-cock 34 and mates with luer connector 88 at the proximal end of catheter 30. Stopcock 34 either blocks flow between tube 28 and catheter 30, permits flow, or connects medication port 32 to catheter 30.

In addition to injecting radiographic material into a patient through catheter 30, system 10 also permits other related functions to be performed. A device for delivering the patient medication (not shown in FIG. 1) may be connected to medication port 32 when medication is to be delivered through catheter 30 to the patient.

When catheter 30 is in place in the patient, and an injection of radiographic contrast material is not taking place, pressure transducer 38 monitors the blood pressure through the column of fluid which extends from catheter 30, tube 28, patient port 84, manifold 26, transducer/saline port 82, tubing 90, T-connector 36, and tubing 92. Transducer 38 has an associated stop-cock 40 which allows transducer 38 to be exposed to atmospheric pressure during calibration and also allows for removal/expulsion of trapped air so the dome chamber of transducer 38 can be flushed with saline.

Peristaltic pump 44 supplies saline solution from bag 50 through saline check valve 46, tubing 42, T-connector 36 and tubing 90 to saline port 82. When peristaltic pump 44 is operating to supply saline solution, the saline solution is supplied through manifold 26 to patient port 84 and then through tube 28 to catheter 30.

Peristaltic pump 44 also operates in an opposite direction to draw fluid from catheter 30 and through tube 28, manifold 26, tubing 90, T-connector 36 and tubing 42 to waste check valve 48 and then into waste collection bag 52.

In a preferred embodiment of the present invention, syringe body 18, manifold 26, tube 28, catheter 30, T-connector 36, tubing 42, check valves 46 and 48, bags 50 and 52, and tubing 90 and 92 are all disposable items. They must be installed in system 10 each time an angiography procedure is to be performed with a new patient. Once system 10 is set up with all the disposable items installed, door 70 is closed, and syringe body 18 filled with contrast material and purged of air, the user (typically a physician) enters into system 10 the safety parameters that will apply to the injection of radiographic contrast material. These safety parameters typically include the maximum amount of radiographic contrast material to be injected during any one injection, the maximum flow rate of the injection, the maximum pressure developed within syringe body 18, and the maximum rise time or acceleration of the injection. To actuate an injection of contrast material, the user operates remote control 14 by squeezing trigger 66. Within the preset safety parameters, system 10 causes the flow rate of the injection to increase as the force or distance of travel of trigger 66 is increased.

Typically, the user will meter the amount and rate of contrast material injected based upon continuous observation of the contrast outflow into the structure being injected using fluoroscopy or other imaging methods. System 10 allows the user to tailor the contrast injections to the needs of the patient, thereby maximizing the quality of the procedure, increasing the safety, and reducing the amount of contrast material required to perform the fluoroscopic examination.

Figure 2B:
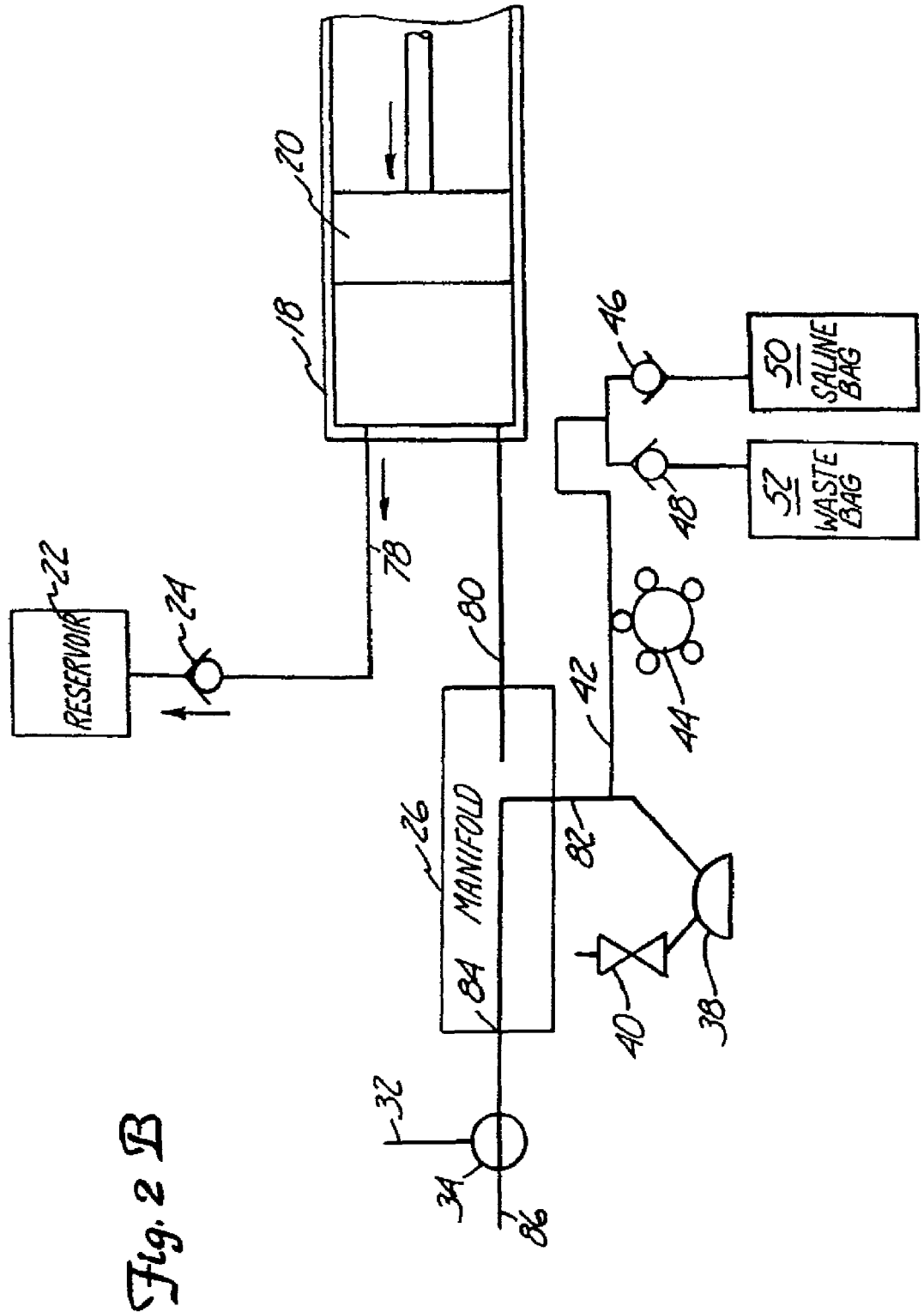

FIGS. 2A-2G are diagrams illustrating fluid flow paths during seven different operations of system 10. Those operational are contrast fill (FIG. 2A), air purge (FIG. 2B), patient inject (FIG. 2C), patient pressure (FIG. 2D), saline flush (FIG. 2E), aspirate waste (FIG. 2F), and medicate patient (FIG. 2G).

The contrast fill operation illustrated in FIG. 2A involves the filling of syringe body 18 with radiographic contrast material from reservoir (contrast media supply) 22. The contrast fill operation is performed during initial set up of system 10, and may be repeated during operation of system 10 whenever syringe body 18 is running low on radiographic contrast material.

During initial set up of system 10, plunger 20 is initially driven to its furthest forward position adjacent closed end 76 of syringe body 18. This will expel to the atmosphere the majority of the air which is located within syringe body 18.

Plunger 20 is then retracted, which creates a vacuum within syringe body 18 which draws contrast material from reservoir 22 through check valve 24 into syringe body 18 through upper port 78.

The Contrast Fill operation typically will result in some air being drawn into or remaining within syringe body 18. It is important, of course, to prevent air from being injected into the patient through catheter 30. That is the purpose of the Air Purge operation shown in FIG. 2B. Also, the location of two ports at different elevations allows for a greater amount of safety in preventing air bubbles in the injection.

During the Air Purge operation, plunger 20 travels forward to expel trapped air within syringe body 18. The air, being lighter than the contrast material, gathers near the top of syringe body 18. As plunger 20 moves forward, the air is expelled from syringe body 18 through upper port 78 and one-way valve 24. In the embodiment illustrated in FIG. 2B, one-way valve 24 is a weighted one-way valve which allows flow of radiographic contrast material from reservoir 22 to upper port 78, but will not allow radiographic contrast material to flow in the opposite direction from upper port 78 to reservoir 22. Valve 24 will, however, allow air to flow from port 78 to reservoir 22. As soon as radiographic contrast material begins flowing out of syringe body 18 through upper port 78 to valve 24, valve 24 closes to prevent any further flow toward reservoir 22.

Valve 24 can also, in alternative embodiments, can be a solenoid actuated or motor driven valve operated under control of the electric circuitry within console 12. In either case, valve 24 is capable to withstanding the relatively high pressures to which it will be subjected during the inject operation. Preferably, valve 24 is capable of withstanding static fluid pressures up to about 1200 p.s.i.

FIG. 2C illustrates the Patient Inject operation. Plunger 20 travels forward under the interactive control of the user, who is controlling trigger 66 of remote control 14. The movement of Plunger 20 creates hydraulic pressure to force contrast material out of syringe body 18 through lower port 80 and through manifold 26 and high pressure tube 28 into catheter 30. As shown in FIG. 2C, syringe lower port 80 and patient port 84 are connected for fluid flow during the patient inject operation.

Manifold 26 contains a valve which controls the routing of fluid connections between patient port 84 and either syringe bottom port 80 or transducer/saline port 82. In one embodiment of the present invention, manifold 26 includes a spool valve which is spring biased so that patient port 84 is normally connected to transducer/saline port 82 (as illustrated in FIGS. 2A and 2B). When the pressure at syringe bottom port 80 builds with the movement of plunger 20 forward, the bias force against the spool valve is overcome so that syringe bottom port 80 is connected to patient port 84, and transducer/saline port 82 is disconnected the valve within manifold 26 protects pressure transducer 38 from being exposed to the high pressure generated by the patient inject operation.

The spool valve opens automatically during the patient inject operation in response to increase pressure exerted on it from the syringe lower port 80. The spool valve closes and returns to its original position allowing for connection of patient port 84 to transducer 38 when a slight vacuum is applied by retraction of plunger 20 at the end of each Patient Inject operation.

In an alternative embodiment, the valve within manifold 26 is an electromechanical or motor driven valve which is actuated at appropriate times to connect either syringe lower port 80 or transducer/saline port 82 to patient port 84. The actuator mechanism is controlled by console 12. Once again in this alternative embodiment, the valve protects pressure transducer 38 from being exposed to high pressure.

FIG. 2D illustrates the Patient Pressure operation. System 10 allows for reading of the patient's blood pressure, which is monitored through catheter 30. Patient blood pressure can be monitored through the use of pressure transducer 38 at any time except during the patient inject, saline flush, and waste aspirate operations. The pressure reading being produced by pressure transducer 38 may be normalized by manually opening stop-cock 40 and closing stop-cock 34 to expose pressure transducer 38 to atmospheric pressure.

During the Saline Flush operation illustrated in. FIG. 2E, saline solution is used to flush all of the internal lines, pressure transducer chamber 38, tube 28, and catheter 30. As shown in FIG. 2E, peristaltic pump 44 is operating in a direction which causes saline solution to be drawn from bag 50 through check valve 46 and through tubing 42 to saline port 82. Manifold 26 connects saline port 82 to patient port 84 so that saline solution is pumped out of patient port 84 and through tube 28 and catheter 30.

During the Aspirate Waste operation, patient port 84 is again connected-to saline port 82. During this operation, peristaltic pump 44 is operating in the opposite direction from its rotation during the saline flush operation. As a result, patient fluids are aspirated from patient port 84 to saline port 82 and then through tubing 42 and check valve 48 into waste collection bag 52. Peristaltic pump 44 acts as a valve pinching/occluding tubing 42 and preventing back flow to/from saline and waste containers 50 and 52 in conjunction with check valves 46 and 48.

With catheter 30 in place within the patient, it may be desirable to supply patient medication. System 10 allows for that option by providing patient medication port 32. As shown in FIG. 2G, when stop-cock 34 is open, a medication source connected to port 32 will be connected to patient port 84, and thereby to catheter 30. During the medicate patient operation, peristaltic pump 44 and plunger 20 are not moving.

Figure 3A:
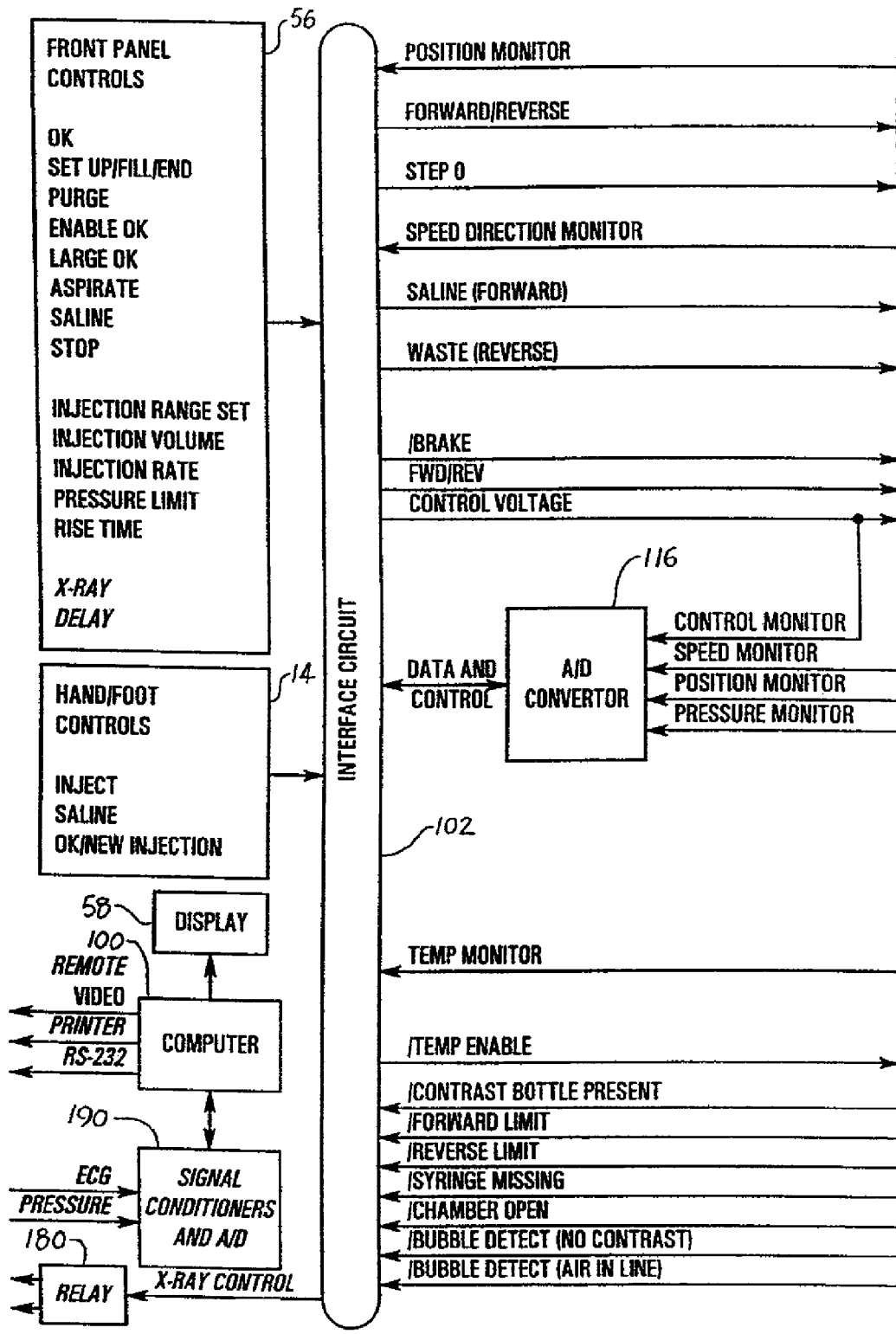
FIG. 3 is an electrical block diagram of the control system of the injector system of FIG. 1.
Figure 3B:
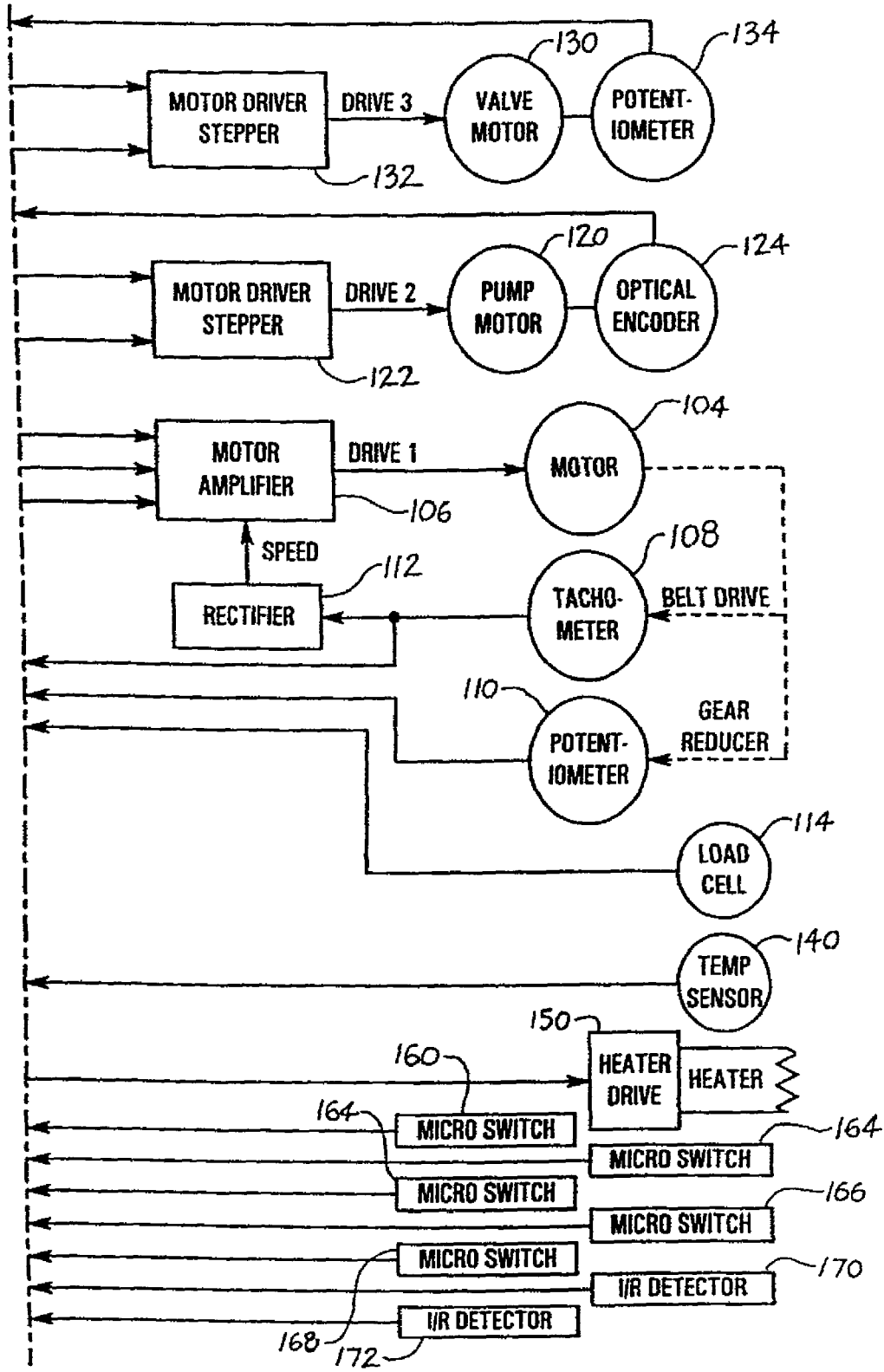

FIG. 3 is an electrical block diagram of the control system which controls the operation of angiographic injector system 10. The electrical control system includes digital computer 100, which receives input signals from remote control 14 and front panel controls 56 through interface 102, and provides signals to display 58 to display operation data, alerts, status information and operator prompts.

Computer 100 controls the motion of plunger 20 through a motor drive circuit which includes motor 104, motor amplifier 106, tachometer 108, potentiometer 110, a rectifier 112, pressure sensing load cell 114, and AM converter 160.

Motor amplifier 106 provides a Drive 1 signal to motor 104 in response to Control Voltage, Fwd/Rev, and/Brake signals from computer 100 and a speed feedback signal from tachometer 108 through rectifier 112. The outputs of tachometer 108 and potentiometer 110 are supplied to computer 100 through A/D converter 116 as Speed Monitor and Position Monitor signals. These allow computer 100 to check motor speed, motor direction, and position (volume is a calculated value).

Pressure sensor 114 senses motor current or plunger force in order to measure the pressure being applied to the radiographic contrast material within syringe body 18. This Pressure Monitor Signal is supplied through A/D converter 116 and interface 102 to computer 100.

Peristaltic pump 44 is driven under the control of computer 100 through pump motor 120, motor driver 122 and optical encoder 124. Computer 100 provides Saline (Forward) and Waste (Reverse) drive signals to motor driver 122 to operate pump motor 120 in a forward direction for saline flush and a reverse direction for waste aspiration. Optical encoder 124 provides the Speed Direction Monitor signal to interface 102 which indicates both the speed and the direction of rotation of pump motor 120.

FIG. 3 illustrates an embodiment of the control system in which valve motor 130 is used to actuate valves such as one-way valve 24 and the valve within manifold 26. In this embodiment, computer 100 controls valve motor 130 through motor driver 132, and monitors position through a Position Monitor feedback signal from potentiometer 134. In this particular embodiment, valve motor 130 is a stepper motor.

Computer 100 monitors temperature of the contrast material based upon a Temp Monitor signal from temperature sensor 140. Temperature sensor 140 is preferably positioned near syringe body 18. If the temperature being sensed by temperature sensor 140 is too high, computer 100 will disable operation motor 104 to discontinue patient injection. If the temperature is too low, computer 100 provides a /Temp Enable drive signal to heater drive 150, which energizes heater 152. In one preferred embodiment, heater 152 is a resistive film heater which is positioned within syringe holder 116 adjacent to syringe body 18.

Computer 100 also receives feedback signals from contrast bottle sensor 160, forward limit sensor 162, reverse limit sensor 164, syringe missing sensor 166, chamber open sensor 168, no contrast bubble detector 170, and air in line bubble detector 172.

Contrast bottle sensor 160 is a miniature switch located within reservoir holder 72. The state of the Contrast Bottle Present signal from sensor 160 indicates whether a reservoir 22 is in position within holder 72. If reservoir 22 is not present, computer 100 will disable the fill operation.

Forward limit and reverse limit sensors 162 sense the end limit positions of plunger 20. When plunger 20 reaches its forward limit position, no further forward movement of plunger 20 is permitted. Similarly, when reverse limit sensor 164 indicates that plunger 20 has reached its reverse limit position, no further reverse movements are permitted.

Syringe missing sensor 166 is a miniature switch or infrared emitter/detector which indicates when syringe body 18 is not in position within syringe holder 16. If syringe body 18 is not in position, all movement functions are disabled except that plunger 20 can move to its reverse limit position (i.e., return to zero).

Chamber open sensor 168 is a miniature switch or infrared emitter/detector which senses when door 70 of syringe holder 16 is open. When the signal from sensor 168 indicates that door 70 is open, all movement functions are disabled. Only when door 70 is closed and locked may any movement be allowed. When door 70 is indicated as closed and sensor 166 indicates the syringe body 18 is in position, other normal functions of the system 10 can proceed.

Bubble detector 170 is positioned between reservoir 22 and top port 78, and is preferably an infrared emitter/detector which senses air bubbles. If an air bubble is sensed in the flow path between reservoir 22 and top port 78 during a fill operation, the fill operation is disabled until a new reservoir is connected.

Bubble detector 172 is positioned to sense air bubbles in high pressure line 28. It is preferably an infrared emitter/detector type of bubble detector. Any air bubble which is sensed in high pressure line 28 results in the disabling of all fluid push out functions, whether the fluid is saline solution from peristaltic pump 44 or contrast material from syringe body 18.

The control system of FIG. 3 also includes the capability to provide a control signal to x-ray equipment through relay 180 which is controlled by computer 100. In addition, computer 100 receives data from blood pressure transducer 38 and from an electrocardiograph (ECG) system, which is separate from injector system 10. The Pressure and ECG signals are received through signal conditioners and A/D converter 190, and are transferred to computer 100. The ECG signal is used by computer 100 in one preferred embodiment, to synchronize operation of motor 104 (and thus the Patient Inject operation) with heart beats.

Blood flow to the heart occurs predominantly in diastole (when the heart is between contractions). Continuous injection of contrast material results in spillage of the contrast material into the aorta during systole (during contraction). By injecting primarily during diastole, contrast dosage can be reduced without impairing the completeness of the contrast injection into the coronary artery.

In a preferred embodiment, the injection of radiographic contrast material is synchronized to the coronary artery blood flow. The time periods of systole and diastole are determined using an electrocardiographic (ECG) electrical signal, arterial blood pressure waveform analysis, or other timing based on the heart rate. By controlling speed of motor 104, speed and therefore movement of plunger 20, the injection of contrast material is interrupted during the period of systole, which reduces or stops contrast injection during this time. In combination with remote control 14, the operator can vary the rate of contrast injection into the coronary artery while computer 100 automatically pulses the contrast injection to the cardiac cycle.

The inertial forces of the moving contrast material and expansion of the containers and tubing holding the contrast material and transmitting it to the patient can cause a phase lag between movement of plunger 20 within syringe body 18 and movement of contrast material out of catheter 30 into the patient. To adjust to the phase lag between the plunger 20 movement and contrast expulsion into the patient, a variable time offset can be entered through control panel 54 such that the timing of the cardiac cycle can be offset by a selected time. Since the magnitude of the phase lag may be dependent on the frequency of the heart rate, an algorithm within computer 100 continuously and automatically adjusts the magnitude of the time offset, based on the instantaneous heart rate during the injection of contrast material.

Figure 4:
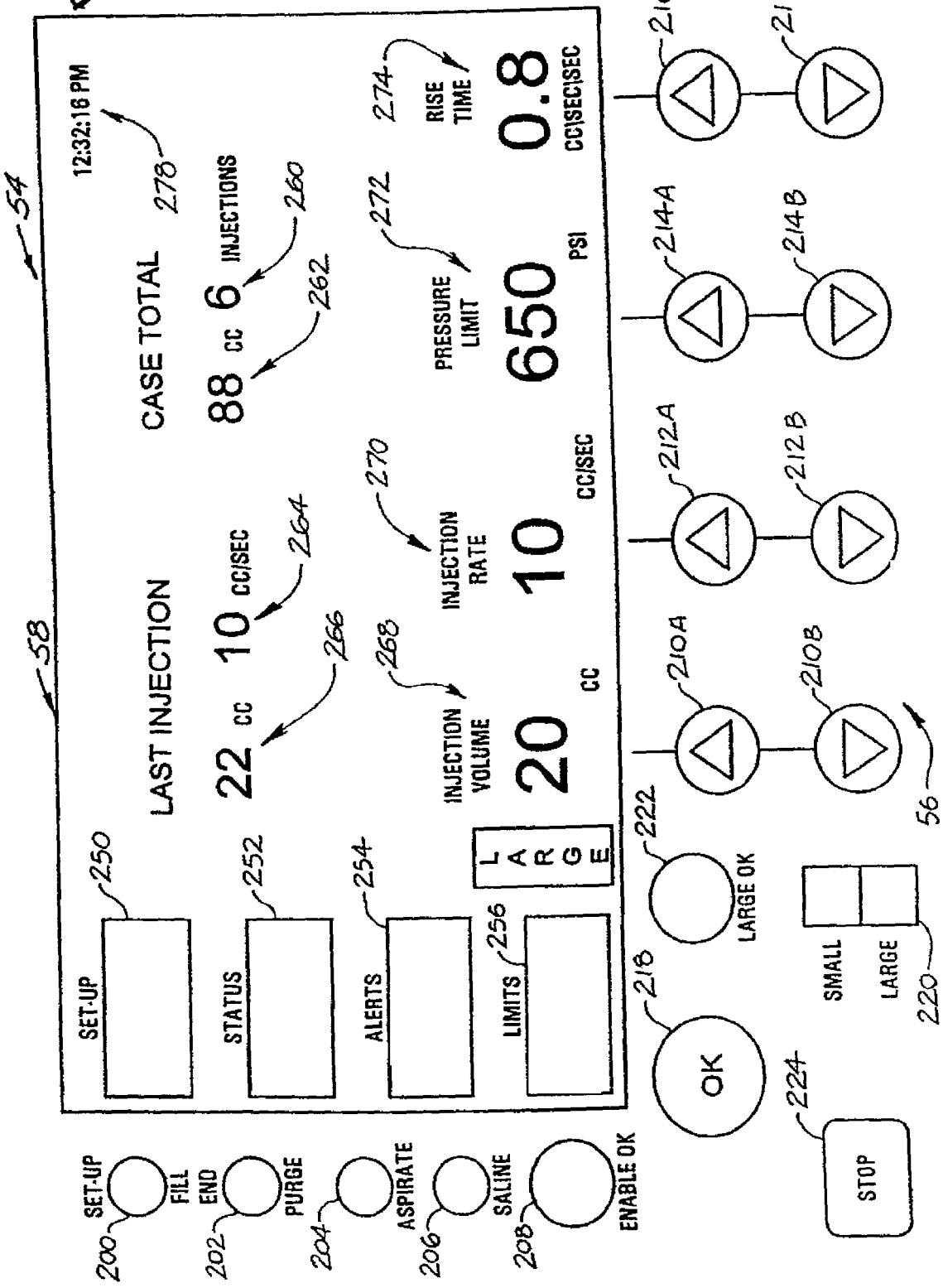
FIG. 4 illustrates front panel controls and displays of a preferred embodiment of the injector system of the present invention.

FIG. 4 shows one embodiment of control panel 54 which illustrates the front panel control switches 56 and display 58 of one embodiment of the present invention. Front panel control switches 56 include Set Up/Fill/End switch 200, Purge switch 202, Aspirate switch 204, Saline switch 206, Enable OK switch 208, Injection Volume Limit switches 210a and 210b, Injection Flow Rate Limit switches 212a and 212b, Injection Pressure Limit switches 214a and 214b, Rise Time switches 216a and 216b OK switch 218, Injection Range Toggle switch 220, Large Injection OK switch 222, and Stop switch 224.

Set Up/Fill/End switch 200 is a momentary push button switch. When it is first activated, the user will be notified to place syringe 18 in syringe holder 16. When syringe 18 has been placed in syringe holder 16 (which is indicated to computer 100 by sensor 166), the user will be instructed to close and lock the chamber (i.e., to close door 70). Plunger 20 is moved to its full forward position expelling all air within the syringe. Display 58 then indicates to the operator that contrast reservoir 22 should be connected. Once contrast reservoir 22 has been put in place, the operator is requested to depress OK switch 218, at which time plunger 20 will retract at a set rate (preferably corresponding to a flow rate of 10 ml per second) to the maximum syringe volume. If the real speed (as indicated by feedback to computer 100 from A/D converter 116) is greater than the set speed, system 10 will stop.

Once plunger 20 is at its rearwardmost position, motor 104 is actuated to move plunger 20 forward to purge all air bubbles. Pressure sensor 114 provides an indication of when one-way valve 24 is closed and pressure is beginning to build up within syringe body 18. Once the purge is completed, the total volume injected and the number of injections counter is reset.

The actuation of switch 200 also allows for Ml retraction and disengagement of plunger 20 from syringe body 18.

Purge switch 202 is a protected momentary push button switch. When activated, Purge switch 202 causes plunger 20 to move forward to expel air through top port 78. The forward movement of plunger 20 is limited and stopped when a predetermined pressure within syringe 18 is reached. This is sensed by pressure sensor 114. The purge operation which is initiated by Purge switch 202 will expel air within syringe 20. The user may also use Purge switch 202 to purge fluid through patient port 84 by depressing and holding Purge switch 202 continuously on.

Aspirate switch 204 is a momentary push button switch which causes computer 100 to activate pump motor 120 of peristaltic pump 44. Pump motor 120 is operated to aspirate catheter 30 at a set speed, with the aspirated fluid being collected in waste bag 52. All other motion functions are disengaged during aspiration. If the real speed of motor 120 is greater than a set speed, computer 100 will stop motor 120.

Saline switch 206 is an alternate action switch. Pump motor 120 is activated in response to Saline switch 206 being pushed on, and saline solution from bag 50 is introduced into manifold 26 and catheter 30 at a set speed. If Saline switch 206 is not pushed a second time to stop the flow of saline solution within 10 seconds, computer 100 automatically stops pump motor 120. If a time-out is reached, Saline switch 206 must be reset to its original state prior to initiating any further actions.

Enable OK switch 208 is a momentary push button switch. After the system has detected a disabling function at the end of an injection other than a limit. Enable OK switch 208 must be activated prior to activating OK switch 218 and initiating any further function.

Injection Volume Limit keys 210a and 210b are pushed to either increase or decrease the maximum injection volume that the system will inject during any one injection. Key 210a causes an increase in the maximum volume value, and key 210b causes a decrease. Once the maximum injection volume limit has been set, if the measured volume reaches the set value, computer 100 will stop motor 104 and will not restart until OK switch 218 has been depressed. If a large injection (i.e., greater than 10 ml) has been selected, OK switch 218 and Large Injection OK switch 220 must both be reset prior to initiating the large injection.

Injection Flow Rate Limit keys 212a and 212b allow the physician to select the maximum flow rate that the system can reach during any one injection. If the measured rate (which is determined by the feedback signals from tachometer 108 and potentiometer 110) reaches the set value, computer 100 will control motor 104 to limit the flow rate to the set value.

Injection Pressure Limit keys 214a and 214b allow the physician to select the maximum pressure that the system can reach during any one injection. If the measured pressure, as determined by pressure sensor 114, reaches the set value, computer 100 will control motor 104 to limit the pressure to the injection pressure limit. The injection rate will also be limited as a result.

Rise Time keys 216a and 216b allow the physician to select the rise time that the system will allow while changing flow rate during any one injection. Computer 100 controls motor 104 to limit the rise time to the set value.

In alternative embodiments, keys 210a-210b, 212a-212b, 214a-214b, and 216a-216b can be replaced by other devices for selecting numerical values. These include selector dials, numerical keypads, and touch screens.

OK switch 218 is a momentary push button switch which resets functions and hardware sensors. In response to OK switch 21.8 being activated, computer 100 controls display 58 to ask the operator to acknowledge that the correct function has been selected. Activation of OK switch 218 causes the status to be set to Ready.

Injection Range switch 220 is a toggle switch. Depending on whether switch 220 is in the "small" or "large" position, it selects either a high or a low injection volume range for the next injection.

Large Injection OK switch 222 is a momentary push button switch. When the large injection range has been selected by injection range switch 220, the Large Injection OK button 222 must be activated to enable OK switch 218. OK switch 218 must be activated prior to each injection. On large volume injections, the user is required to verify the volume selected by activating first Large Injection OK switch 222 and then OK switch 218.

Stop switch 224 is a momentary push button switch. When stop switch 224 is pushed, it disables all functions. Display 58 remains active.

Display panel 58 includes Set-Up display 250, Status display 252, Alerts display 254, Limits display 256, total number of injections display 260, total volume injection display 262, flow rate display 264, injection volume display 266, injection volume limit display 268, injection rate limit display 270, pressure limit display 272, rise time minimum display 274, large injection display 276, and real time clock display 278.

Set-Up display 250 contains a series of messages which are displayed as the operator goes through the set up procedure. The display of messages in set up display 250 are initiated by the actuation of set up switch 200 as described previously.

Status display 252 provides a flashing indication of one of several different operating conditions. In the embodiment shown in FIG. 4, these status conditions which can be displayed include "Ready", "Set-Up", "Injecting", "Filling", "Flushing", and "Aspirating".

Alerts display 254 and Limits display 256 notify the operator of conditions in which system 10 has encountered a critical control parameter and will disable operation, or has reached an upper or lower limit and will continue to function in a limited fashion, or has reached an upper or lower limit and will continue to operate.

Total number of injections display 260 displays the total number of injections (cumulative) given for the current patient case. The cumulative total volume injected during the current patient case is displayed by total volume display 262.

Displays 264 and 266 provide information on the current or last injection. Display 264 shows digital value of the real time flow rate to the patient during injection. Once the injection is completed, the value displayed on display 264 represents the peak flow rate reached during that injection. Display 266 shows the digital value of the volume injected during the most recent injection.

Display 268 displays the digital value of the maximum injection volume selected by operation of switches 210a and 210b. Similarly, display 270 shows the digital value of the maximum flow rate that the system will allow, as selected by switches 212a and 212b.

Display 272 shows the digital value of the maximum pressure that the system will allow to be developed in syringe 18. The pressure limit is selected by switches 214a and 214b.

Display 274 displays the minimum rise time that the system will allow while changing flow rate. The minimum rise time is selected through switches 216a and 216b.

Large injection display 276 provides a clear indication when the large injection scale has been selected by the operator.

Real-time clock display 278 shows the current time in hours, minutes, and seconds.

Figure 5A:
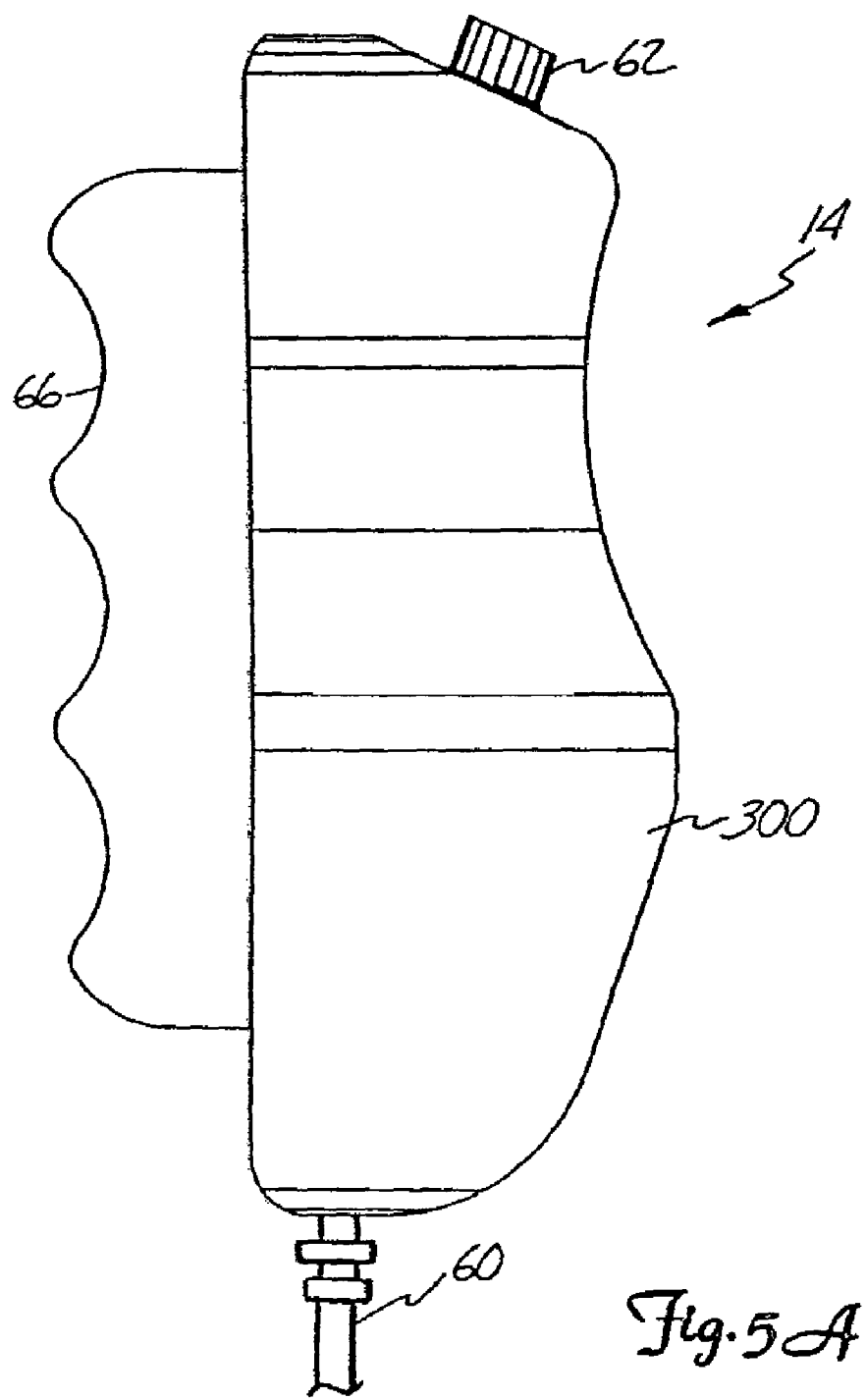
FIGS. 5A and 5B are side and partial top perspective views of the remote control of the system of FIG. 1.
Figure 5B:
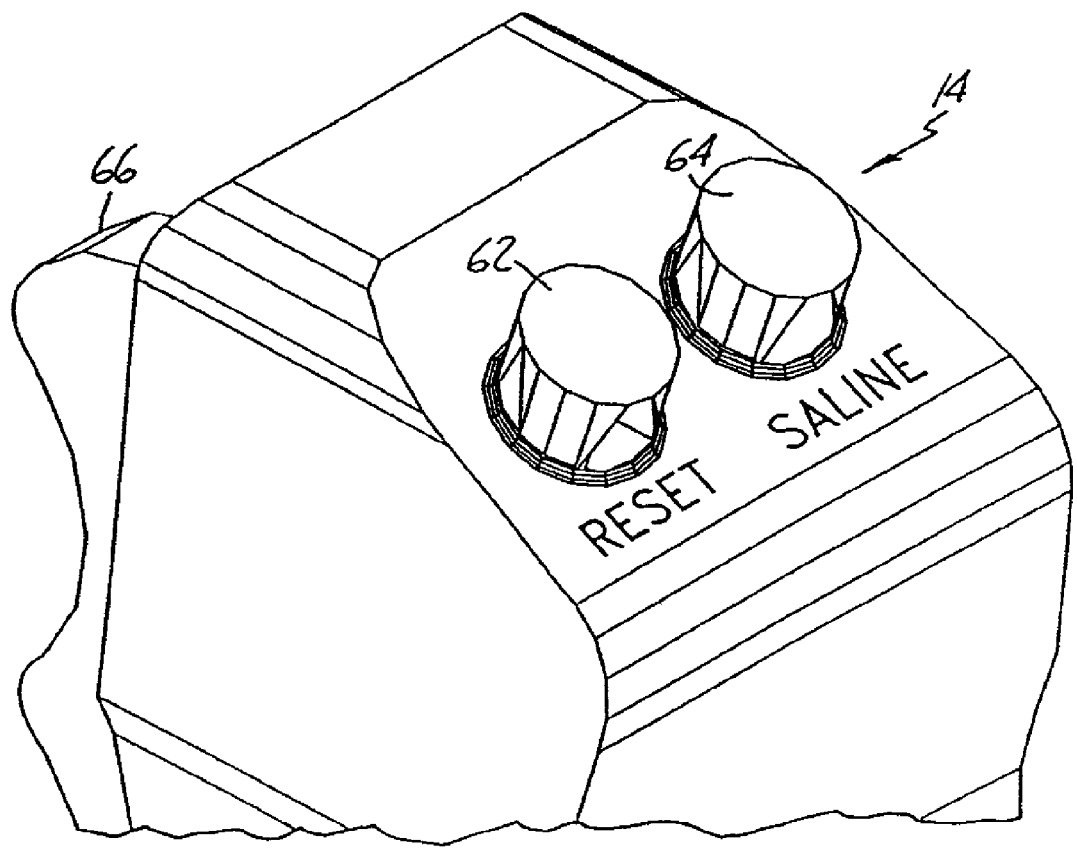
Figure 6:
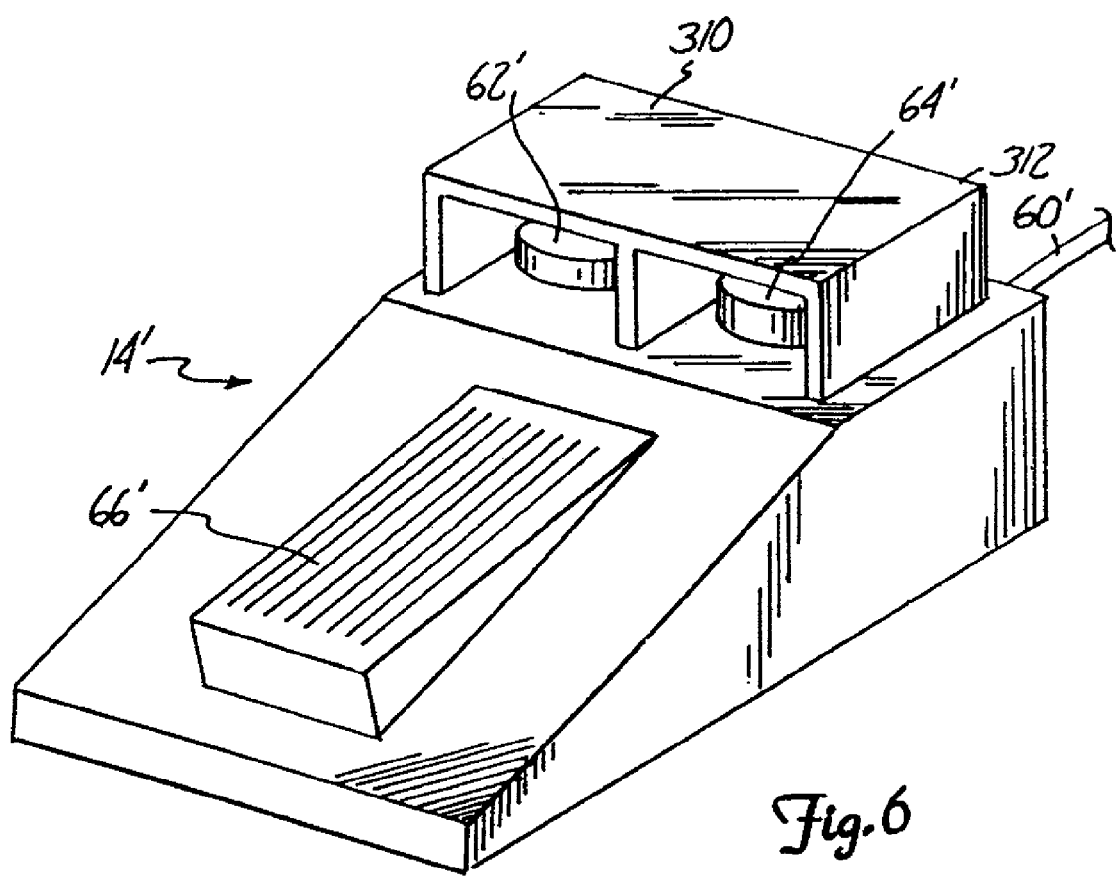
FIG. 6 is a perspective view of a foot operated remote control.

FIGS. 5A and 5B show remote control 14 which includes main housing 300, which is designed to conform to the users hand. Trigger 66 is movable with respect to housing 300, and the position of trigger 66 generates a command signal which is a function of trigger position. In one embodiment, trigger 66 is linked to a potentiometer within housing 300. The command signal controls the injunction flow rate or speed. The flow rate is directly proportional to trigger position.

Reset switch 62 is a momentary push button switch whose function is identical to that of OK switch 218. Alternatively, Reset switch 62 may also be labeled "OK".

Saline switch 64 on remote control 14 is an alternate action push button switch which is pushed to turn on and pushed again to turn off. The function of Saline switch 62 is the same as that of Saline switch 206 on front panel 54.

As illustrated in another embodiment of the present invention, an alternative remote control 14' in the form of a foot pedal is used instead of the hand held remote control 14 illustrated in FIG. 1 and in FIGS. 5A and 5B. Foot pedal remote control 14' includes foot operated speed pedal or trigger 66' for providing a command signal, as well as Reset or OK switch 62' and Saline switch 64'. Covers 310 and 312 protect switches 62' and 64' so that they can only be actuated by hand and not accidentally by foot. Foot pedal remote control 14' is connected to console 12 by cable 60', but could alternatively be connected by a wireless link.

FIGS. 7A-7D and FIGS. 8A-8C illustrate the construction and operation of one way valve 24 and manifold 26 during Contrast Fill, Air Purge and Patient Injection operation.

FIGS. 7A and 8A illustrate one way or check valve 24, manifold 26, syringe body 18, and plunger 20 during a Contrast Fill operation. Inlet check valve of one way valve 24 includes weighted ball 350 which is positioned at its lower seated position within valve chamber 352 in FIGS. 7A and 7B. Contrast material is being drawn into syringe body 18 by the rearward movement of plunger 20. The contrast material flows through passages 354 around ball 350 and into upper port 78.

Manifold 26 contains spring loaded spool valve 360, which includes spool body 362, shaft 364, O-rings 366, 368 and 370, bias spring 372, and retainer 374. As shown in FIG. 7A, during the Contrast Fill operation, bias spring 372 urges spool body 362 to its right-most position toward syringe body 18. In this position, spool body 362 blocks lower port 80 of syringe body 18 while connecting transducer saline port 82 to patient port 84 through diagonal passage 376. O-rings 366 and 368 on the one hand, and O-ring 370 on the other hand, are positioned on the opposite sides of diagonal passage 376 to provide a fluid seal.

FIGS. 7B and 8B illustrate the Air Purge operation. Syringe body 18 has been filled with contrast fluid, but also contains trapped air. Plunger 20 is driven forward to force the air out of syringe body 18 through upper port 78 and through check valve 24. The force of the air may cause a slight lifting of ball 350 in check valve 20. Ball 350, however, is sufficiently heavy that the air being forced out of syringe body 18 and back toward reservoir 22 cannot lift ball 350 into its uppermost seated position where it would block the flow of air out of syringe body 18.

During the Air Purge operation, spool valve 360 is in the same position as in FIG. 7A. Diagonal passage 376 connects transducer saline port 82 with patient port 84. As a result pressure monitoring by pressure transducer 38 can be performed during the Air Purge (as well as the Contrast Fill) operation.

FIGS. 7C and 8C illustrate the state of manifold 26 and check valve 24 at the end of the Air Purge operation and at the beginning of a Patient Inject operation.

In FIG. 7C, all air has been expelled from syringe body 18. Ball 350 may float on the radiographic contrast material, so that when all air has been removed and the radiographic contrast material begins to flow out of syringe body 18 and through upper port 78 to valve chamber 352, ball 350 is moved upwards to its upper seated position. Ball 350 blocks any continued upward flow of radiographic contrast material, as is illustrated in FIGS. 7C and 8C.

In the state which is illustrated in FIG. 7C, the pressure within syringe body 18, and specifically the pressure in lower port 80 has not yet reached a level at which the bias force of spring 372 has been overcome. As a result, spool body 362 has not yet moved to the left and diagonal passage 376 continues to connect transducer saline port 82 with patient port 84.

Figure 7D:
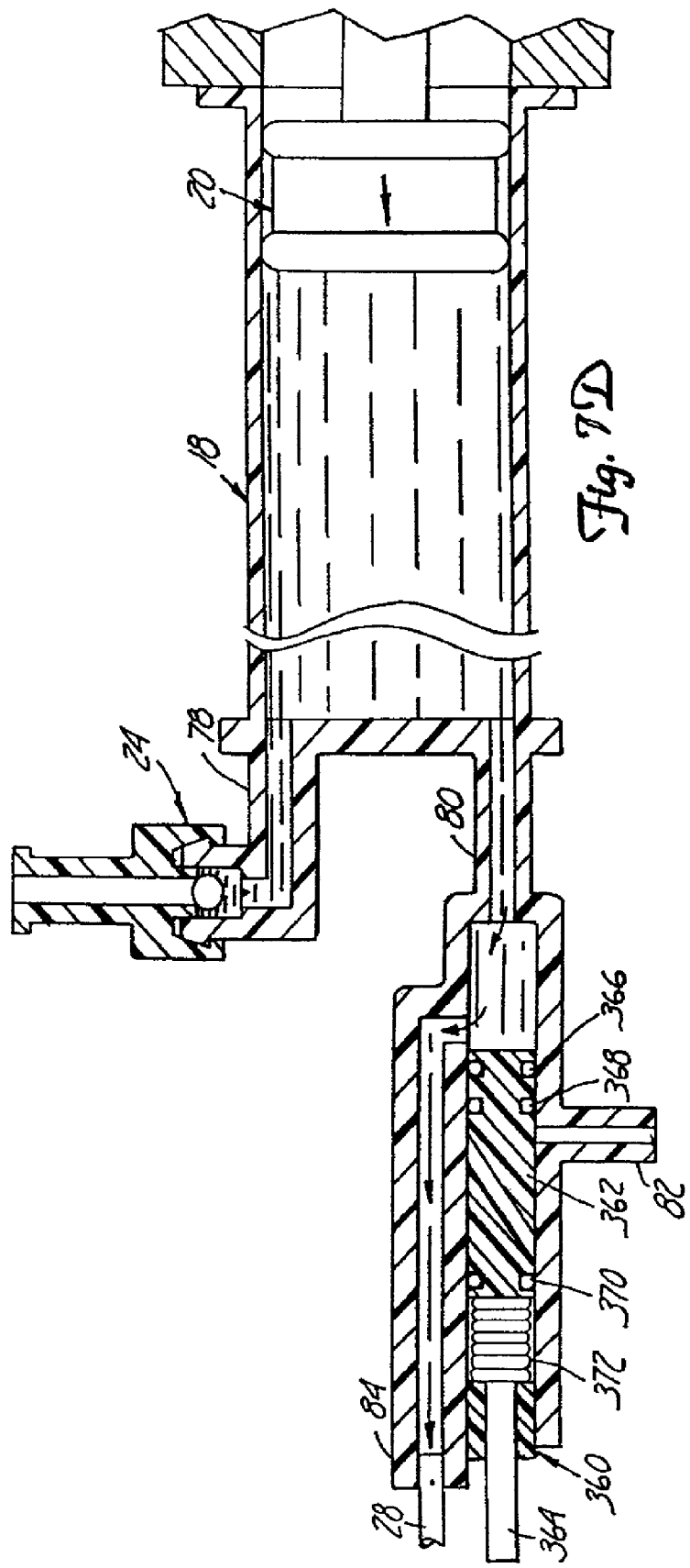

FIG. 7D illustrates the patient inject operation. Plunger 20 is moving forward, and inlet check valve 24 is closed. The pressure at lower port 80 has become sufficiently high to overcome the bias force of spring 372. Spool body 362 has been driven to the left so that lower port 80 is connected to patient port 84. At the same time spool body 362 blocks transducer/saline port 82.

By virtue of the operation of spool valve 360, the high pressure generated by movement of plunger 20 and syringe body 18 is directly connected to patient port 84, while saline port 82 and pressure transducer 38 are protected from the high pressure. The pressure to actuate may be variable and determined after manufacture by increasing or decreasing the syringe preload.

B. Detailed Description of the Present Invention

Figure 9:
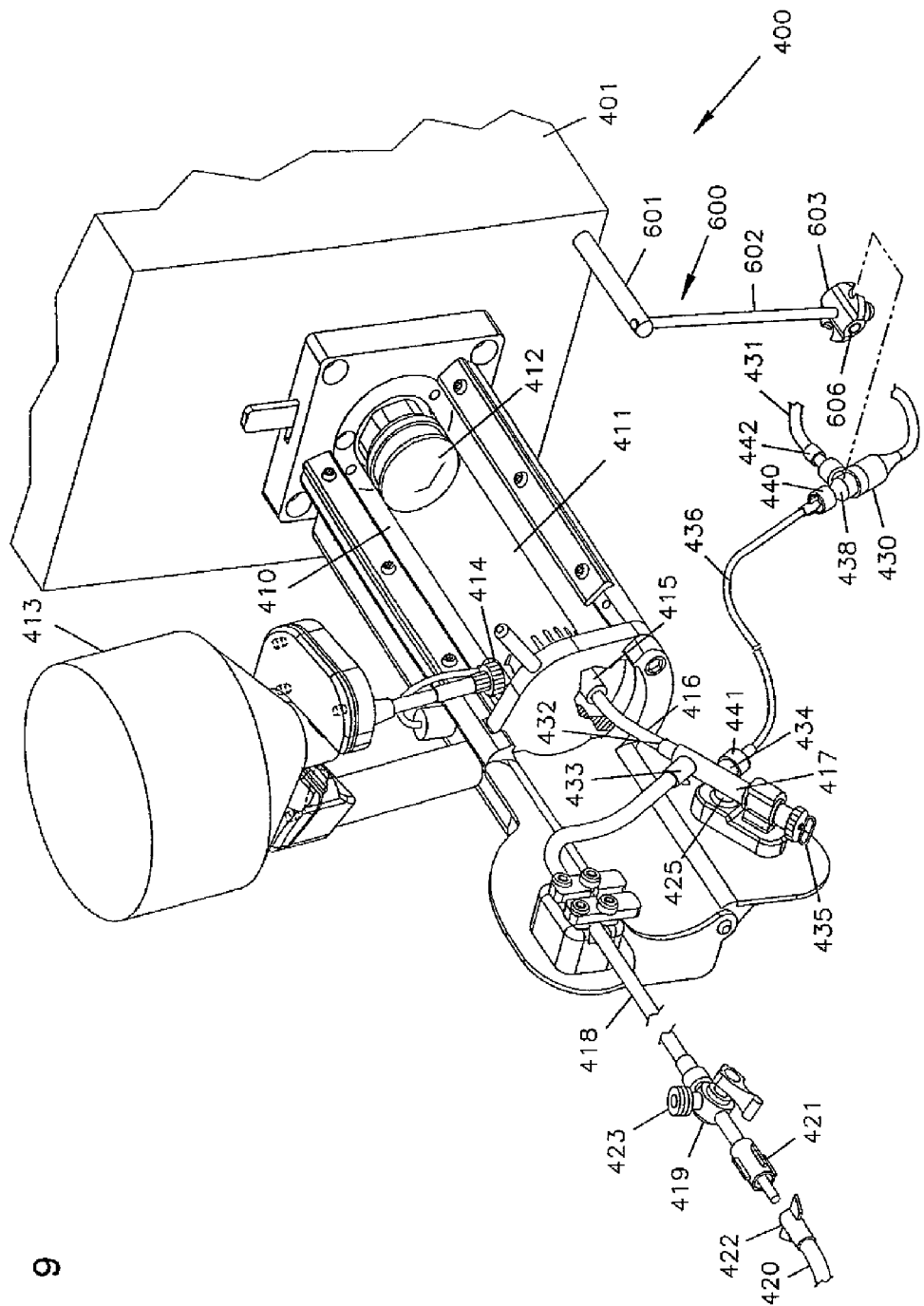
FIG. 9 is a perspective view illustrating a preferred embodiment of a portion of the angiographic injector system of the present invention.

FIG. 9 illustrates another embodiment for an injector system 400 according to the invention. According to this embodiment, system 400 includes a main console 401, syringe holder 410, syringe body 411, syringe plunger 412, radiographic material reservoir 413, one-way valve 414, lower port 415, lower port tube 416, manifold assembly 417, patient tube 418, three-way stopcock 419, catheter 420 and transducer 430. Tubing 431 is similar to tubing 42 of the previously described embodiments and provides for saline flush or waste removal. In addition, the previously described peristaltic pump, saline check valve, waste check valve, saline bag, waste bag, bag support rack, counsel and remote control previously described can be used in the present embodiment.

Lower port 415 of syringe body 411 is connected to manifold assembly 417 through high pressure port 432 optionally using lower port tube 416. Manifold assembly 417 includes a spring bias spool valve as described below. The spring bias spool valve can be manually operated by handle 435. During low pressure operation, manifold assembly 417 provides a fluiditic connection from low pressure port 434 to patient port 433. During high pressure operation, manifold assembly 417 provides a fluiditic connection from high pressure port 432 to patient port 433. Hence, during a patient inject operation, the pressure of injection of the radiographic material causes the spool valve in manifold assembly 417 to change from the low pressure position to the high pressure position such that lower port 415 is in fluid flow communication with patient port 433.

In some embodiments, the spring bias spool valve which controls routing of fluid flow through manifold assembly 417, can be manually operated by pulling or pushing handle 435. According to the illustrated embodiment, moving handle 435 away from manifold assembly 417 changes fluid flow from the low pressure path (i.e., low pressure port 434 to patient port 433) to the high pressure path (i.e., high pressure port 432 to patient port 433).

Patient tube 418 can be a flexible tube which connects patient port 433 to catheter 420. A three-way stopcock 419 can be located at the distal end of patient tube 418. Rotatable lure lock connector 421 mates with lure connector 422 at the proximal end of catheter 420. Stopcock 419 either permits or blocks flow between patient tube 418 and catheter 420, or connects medication port 423 to catheter 420. As described earlier, a device for delivering patient medication may be connected to medication port 423.

When catheter 420 is in place in the patient, and an injection of radiographic contrast material is not taking place, i.e., low pressure operation, pressure transducer 430 monitors the blood pressure through the column of fluid which passes through catheter 420, patient tube 418, patient port 433, manifold assembly 417, low pressure port 434, low pressure tube 436, and dome chamber 438. Transducer connector 440 couples a first end of low pressure tube 436 to transducer 430 and low pressure connector 441 couples a second end of low pressure tube 436 to low pressure port. As illustrated in FIG. 9, flush tube 431 can mount to transducer 430 through flush tube connector 442. In some embodiments, system 400 can also include a transducer holder 600 (discussed below) for adjustable positioning of transducer 430. When a peristaltic pump, discussed earlier, is operating to supply saline solution through flush tube 431, the solution is supplied through manifold assembly 417 to patient port 433 and then through patient tube 418 to catheter 420. It will be appreciated that aspiration applied at low pressure port 434 can draw blood from the patient through patient tube 418, manifold assembly 417, low pressure port 34 and into flush tube 431.

In the present embodiment, preferably, syringe body 411, manifold assembly 417, patient tube 418, catheter 420, stopcock 423, low pressure tube 436, transducer dome chamber 438, flush tube 431 and previously described check valves, fluid containers and waste containers are all disposable items. They should be installed in system 400 each time a new procedure is to be performed with a new patient. Once system 400 is set up with all the disposable items installed, the operator enters into the console 401 of system 400, the limiting safety parameters that will apply to the patient injection of radiographic contrast material.

Figure 13:
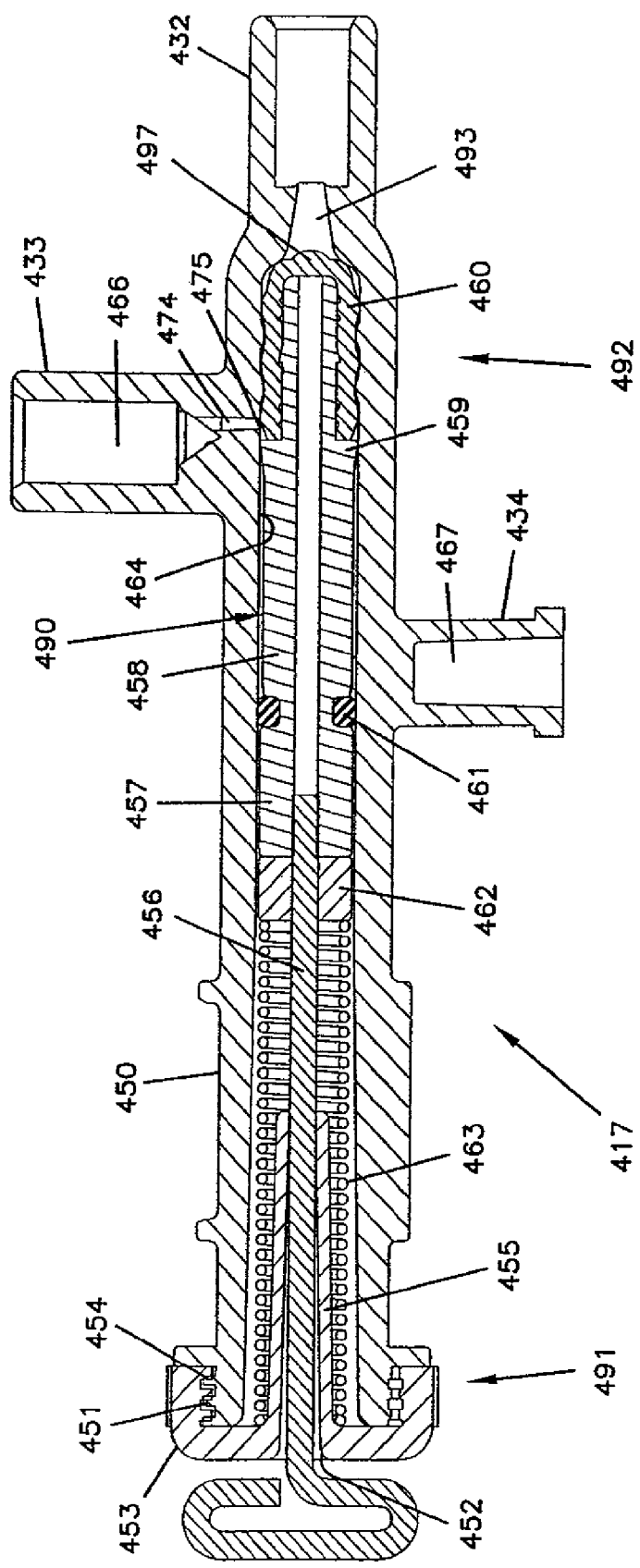
FIG. 13 is a longitudinal cross section view of one embodiment of a manifold assembly according to the invention.

FIGS. 10-18 illustrate preferred embodiments of a manifold assembly 417. FIG. 10 is a side view of one embodiment of the shell (body) 450 of manifold assembly 417; FIG. 11 is a top view of manifold shell 450; FIG. 12 is a bottom view of manifold shell 450; and FIG. 13 is a longitudinal cross section view of manifold assembly 417. These figures all illustrate high pressure port 432, patient port 433 and low pressure port 434.

FIG. 13 illustrates that manifold handle 435 has a shaft 456 that passes through opening 452 of manifold cap 453. Manifold cap 453 has threads 454 for securing cap 453 to first end 491 of manifold shell 450 through manifold shell threads 451. In the illustrated embodiment, cap 453 includes a hollow protuberance 455 through which handle shaft 456 passes into manifold 450. Manifold plunger assembly 490 includes, manifold shaft 458, manifold wiper 460, O-ring 461 and valve sensor trigger 462. Protuberance 455 of manifold cap 453 stops travel of manifold plunger assembly 490 to the left (relative to the orientation of FIG. 13) during high pressure operation. Spring 463 is mounted over handle shaft 456 between manifold cap 453 and valve sensor trigger 462 to maintain a fluiditic connection between low pressure port 434 and patient port 433.

Within manifold assembly 417, handle shaft 456 is rigidly fixed to a first end 457 of manifold shaft 458 using, for example, threads. Manifold wiper 460 is mounted at the second end 459 of manifold shaft 458. In the illustrated embodiment, manifold shaft 458 has a hollow core that is open at first end 457 and second end 459. The hollow core provides for release of air that would otherwise be trapped inside the hollow region of manifold wiper 460 during assembly. In the illustrated embodiment, wiper 460 includes a thickened tip 497 which provides reinforcement of the wall of wiper 460 to reduce the chance of rupture of wiper 497 into the hollow core of manifold shaft 458. Preferably, manifold wiper 460 is manufactured from an elastomeric thermoset material, for example, ethylene propylene diene monomer (EPDM) silicon, nitrile, polyisoprene, etc. The resistance to compression set of the thermoset material provides for maintaining a fluid tight seal between the outer perimeter of manifold wiper 460 and the inner surface 464 of manifold shell 450.

A valve sensor trigger 462 is mounted at the first end 457 of manifold shaft 458. The position of the valve sensor trigger 462 is detected by the valve state sensor 425 (FIG. 9) to indicate the state of the fluiditic connections within manifold assembly 417. In one embodiment, the valve state sensor trigger 462 can be manufactured from stainless steel for use with an inductive type valve state sensor 425.

Figure 13A:
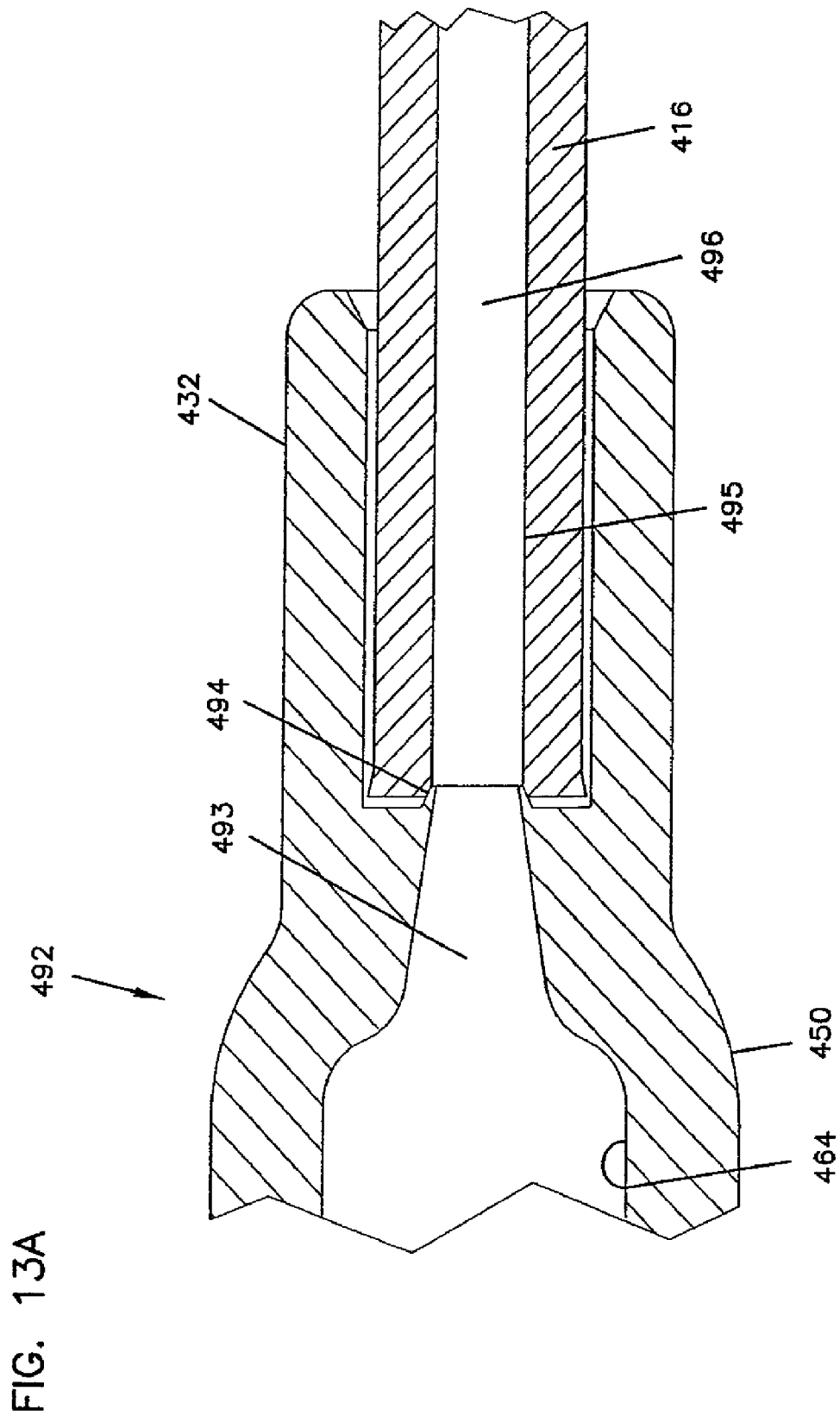
FIG. 13A is a longitudinal cross section view of one end of the manifold shell of FIG. 13.

FIG. 13A illustrates a longitudinal cross section view of the second end 492 of manifold shell 450 of FIG. 13. As illustrated in FIG. 13A, the inner surface 464 of shell 450 near high pressure port 432 is cone shaped 493. This cone shaped end 493 provides a gradual transition from high pressure port 432 to inner surface 464 which can facilitate removal of trapped air at this junction during initial flushing of the system by minimizing adverse turbulent flow. In addition, the cone shaped end can eliminate regions of fluid stagnation during injection. In addition, the external configuration of the cone tip protrudes slightly and is wedge shaped to form an annular ring 494 for an air tight pressure fit with the inner surface 495 of lumen 496 of low port tube 416.

Referring to FIGS. 10-17, the structure of manifold shell 450 at the junction between the inner surface 464 of manifold shell 450 and the fluid channel 466 of patient port 433 and the fluid channel 467 of low pressure port 434 will be described.

Figure 14A:
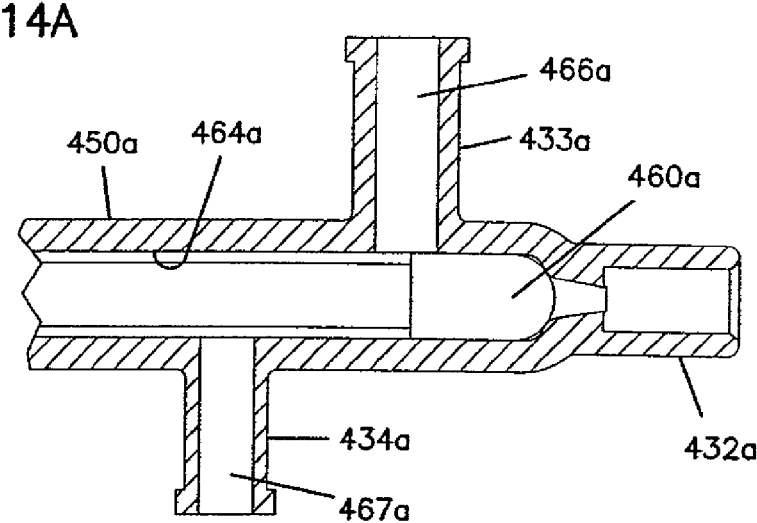
FIGS. 14A-C are longitudinal cross section views which sequentially illustrate the interaction of an elastomeric wiper and the inner surface of a manifold shell as the wiper moves from its low pressure position to its high pressure position.
Figure 14B:
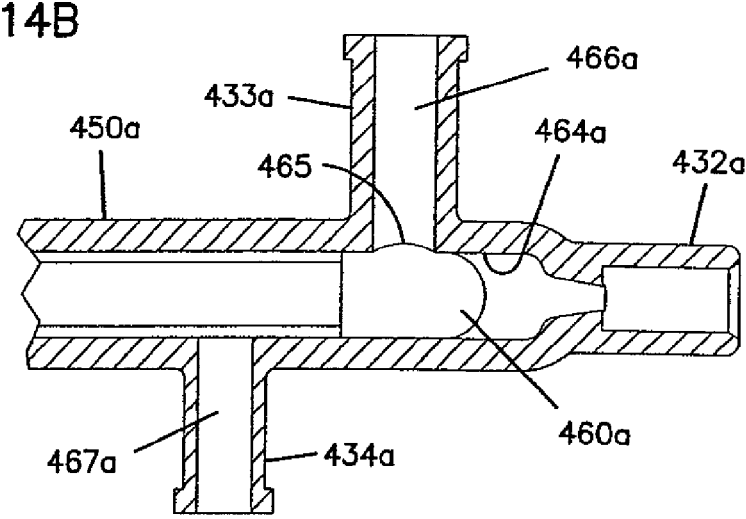
Figure 14C:
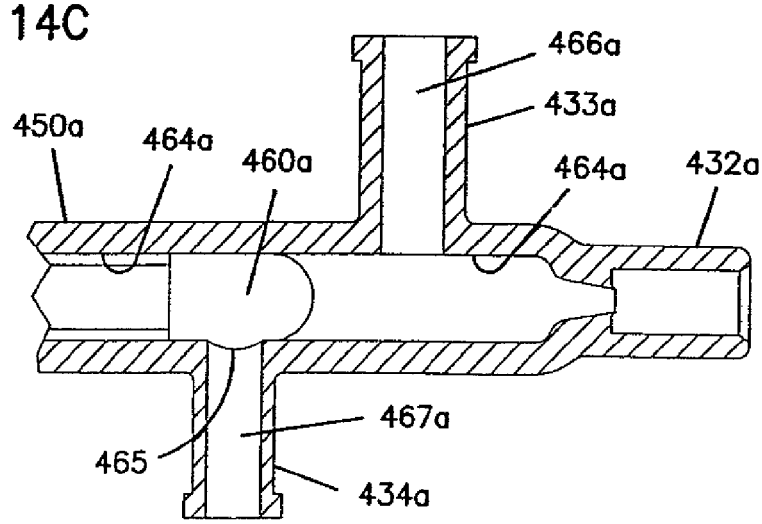

FIGS. 14A-C are longitudinal cross section views which illustrate the interaction of an elastomeric manifold wiper 460a and the inner surface 464a of a manifold shell 450a as the wiper 460a moves from its low pressure position (FIG. 14A) to its high pressure position (FIG. 14C. As illustrated in FIG. 14B as wiper 460a moves within the inner surface 464a of manifold shell 450a past fluid channel 466a of patient port 433a, the elastomeric material of wiper 460a tends to "extrude" (illustrated as 465) into the fluid flow channel 466a of patient port 433a. The same event can occur as wiper 460a passes over fluid flow channel 467a of low pressure port 434a (FIG. 14C). A potential problem with extrusion of wiper 460a into fluid flow channels, 466a or 467a, is that the extruded portion 465 of manifold wiper 460a can prevent proper functioning of manifold assembly 417 by causing plunger assembly 490 to stick in a position wherein wiper 460 blocks fluid channels 466a or 467a. In addition, the extruded portion 465 can be broken or "nibbled" off during passage of wiper 460a past fluid channels 466a or 467a. In a preferred embodiment, manifold assembly 417 is constructed to reduce the amount of extrusion and reduce the likelihood of sticking or nibbling of manifold wiper 460 as it moves past fluid channels 466 and 467.

FIG. 11 is a top view of manifold shell 450 looking down into fluid flow channel 466 of patient port 433. FIG. 15 is a transverse cross section view through line 15 of FIG. 11. FIG. 12 is a bottom end view of manifold shell 450 looking into fluid channel 467 of low pressure port 434. FIG. 16 is a transverse cross section view through line 16-16 of the low pressure port of FIG. 12. Referring to patient port 433 in FIGS. 11 and 15, at the location where fluid channel 466 communicates with the inner surface 464 of manifold shell 450, the fluid channel 466 is bifurcated by a "fillet" 468 to form a multipartate opening. As illustrated best in FIG. 15, fillet 468 permits fluid flow through elongate openings 469a and 469b of shell 450 into fluid channel 466 but also constrains expansion of manifold wiper 460 to reduce the amount of extrusion into fluid channel 466. Preferably, fillet 468 reduces the likelihood of extrusion of manifold wiper 460 into fluid channel 466, but does not cause an increase in cavitation or an appreciable increase in resistance to the flow of fluid passing into fluid channel 466. It will be appreciated that openings 469a and 469b are not limited to any particular shape as a result of the fillet. Moreover, while FIGS. 11 and 15 show a single fillet creating two openings, additional fillets forming more than two openings are envisioned within the scope of the invention. In the illustrated embodiment, the opening is bipartate and the longitudinal dimension of the fillet is oriented parallel to the longitudinal dimension of the manifold shell 450. Also, in one embodiment, the fillet is about 0.030 inch wide, the longitudinal dimension of openings 469a and 469b is about 0.080 inch and the width of openings 469a and 469b is about 0.030 inch.

Referring now to FIGS. 12 and 16, for the reasons discussed above, a similar fillet 470 can be present in fluid flow channel 467 of low pressure port 434, bifurcating channel 467 into opening 471a and 471b.

Figure 17:
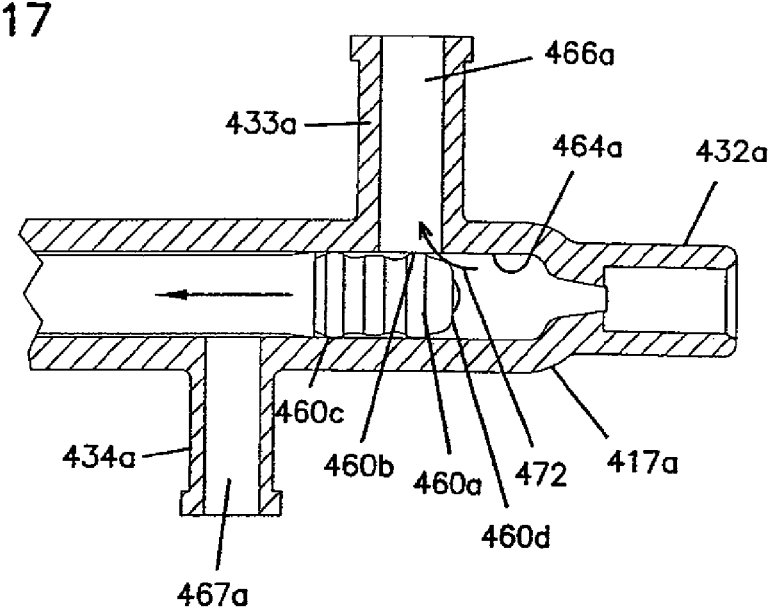
FIG. 17 is a diagrammatic illustration of a temporal position of a manifold plunger between the low pressure position and the high pressure position.

FIG. 17 diagrammatically illustrates a temporal position of manifold wiper 460a at a position after which the pressure at high pressure port 432a has become sufficient to overcome: (1) the bias force of spring 463 (FIG. 13); (2) the friction force between manifold wiper 460a and manifold inner surface 464a; (3) the pressure induced friction force between seal ring 460b and manifold inner surface 464a. In the illustration, manifold wiper 460a has not moved completely to the left to the fully open high pressure position. Just after seal ring 460c has blocked the fluid connection between patient port 433a and low pressure port 434a, the pressurized fluid entering high pressure port 432a can flow up fluid channel 466a, at arrow 472, which reduces the pressure at high pressure port 432a because there is, as yet, little flow resistance or pressure build up in fluid channel 466a.

This reduction in pressure simultaneously reduces the pressure induced force on the seal face 460d and pressure induced friction force between seal ring 460b and manifold inner surface 464a. Without being limited to a single theory, it is believed that as the forces pushing and holding the plunger assembly 490 to the left are simultaneously reduced, the force of spring 463 must also decline due to the laws of physics. Thus, spring 463 must expand, which pushes plunger assembly 490 to the right. Once manifold wiper 460a moves far enough to the right to seal off the fluid outflow through fluid flow channel 466a, the pressure at high pressure port 432a will increase again to overcome the bias force of spring 463 allowing wiper 460a to move enough to the left to allow fluid to once again rush out at arrow 472. The repeated occurrence of the movement of wiper 460a back and forth at the point where fluid is just beginning to move up fluid channel 466a at arrow 472 results in an oscillation of the plunger. This oscillation can produce a pulsation in the fluid flow which causes uncontrolled variable flow rates.

Referring to FIGS. 11, 13 and 18, in a preferred embodiment of the invention, manifold assembly 417 is constructed, in part, to reduce or eliminate the occurrence of this oscillation. FIG. 18 is a transverse sectional view taken at line 18-18 of FIG. 11. Referring to FIGS. 11 and 18, within patient port 433, there is located an outer oscillation reduction port 473. The port 473 leads into an oscillation reduction channel 474 that extends from patient port 433, through manifold shell 450 to communicate with the inner surface 464 of manifold shell 450 at inner oscillation reduction port 475 (FIGS. 13 and 18). Referring to FIG. 13, during use, as the pressure at high pressure port 432 becomes sufficiently high to overcome the previously described counter forces, manifold wiper 460 moves to the left. As wiper 460 moves sufficiently to the left to expose inner port 475 of oscillation reduction channel 474, fluid is forced up oscillation reduction channel 474. The resistance to fluid flow from the combination of inner port 475 and oscillation reduction channel 474 is sufficient to maintain the pressure within the inner surface 464 of manifold assembly 417 to prevent oscillation. This maintained pressure also maintains the pressure induced force on seal face 460d. As a result, plunger assembly 490 is moved fully to the left without oscillation. Thus, oscillation ports 473 and 475 and oscillation channel 474 maintain the force balance between the biasing spring 463 and the pressure induced force of the fluid on wiper 460.

Figure 19:
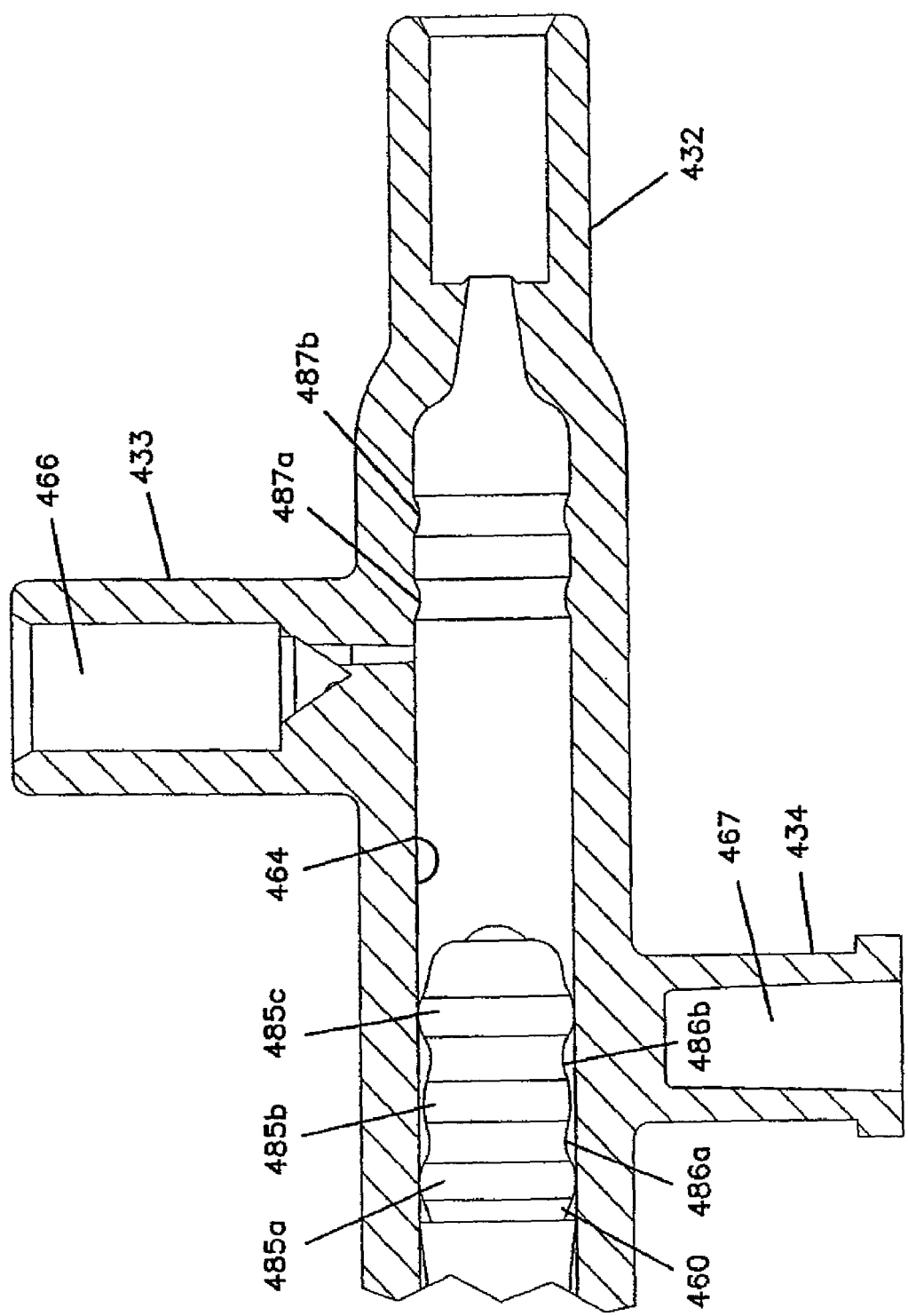
FIG. 19 is a longitudinal cross section view of one embodiment of a manifold shell according to the invention.
Figure 19A:
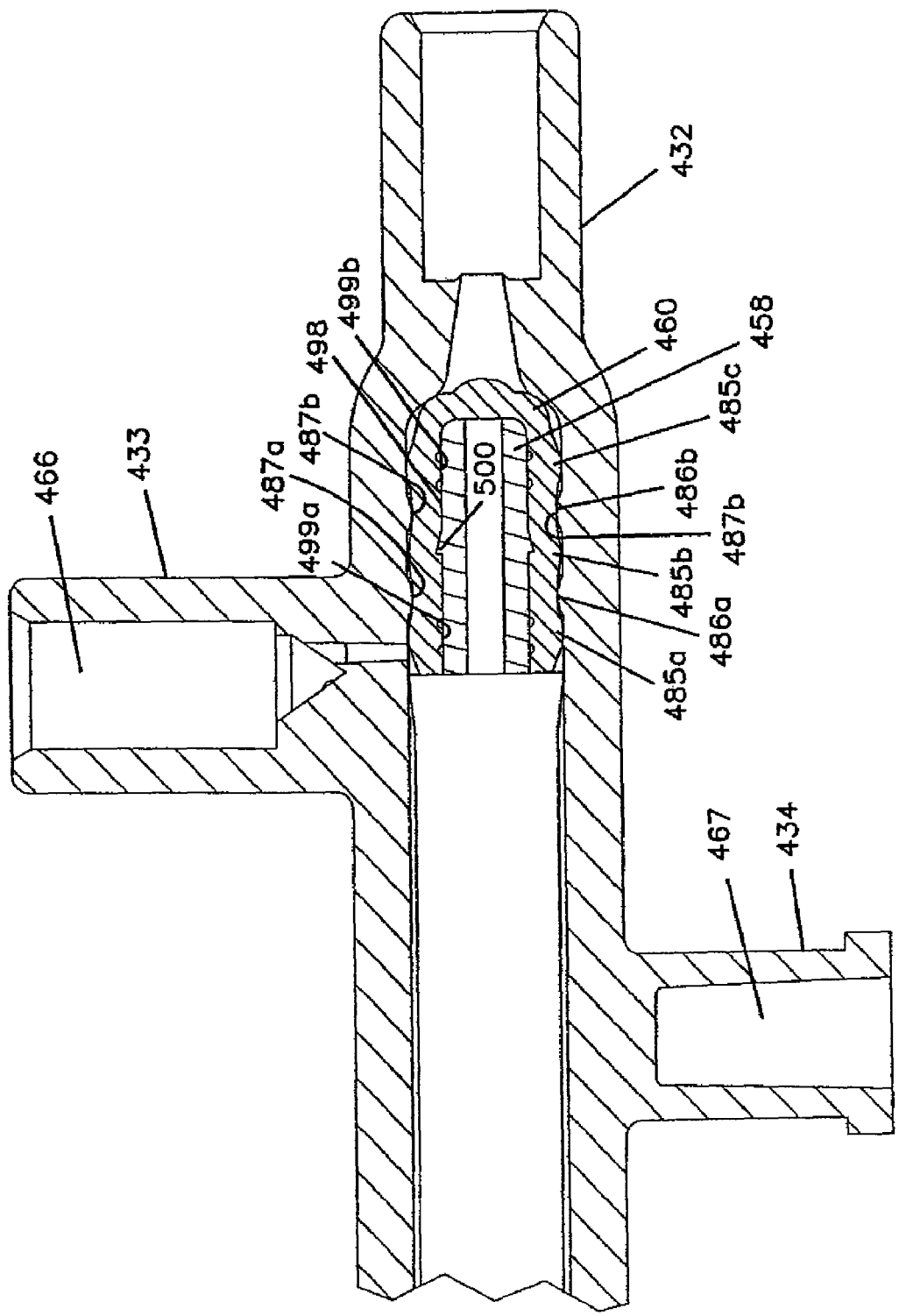
FIG. 19A is a longitudinal cross section view of the embodiment of FIG. 19 with the plunger wipe view in cross section and at a different position within the manifold shell.

Referring to FIGS. 19 and 19A, in some embodiments, the elastomeric material of manifold wiper 460 can be configured to form a plurality of ridges, 485a, 485b and 485c. These ridges contact inner surface 464 of manifold shell 450. In one aspect, the intervening valleys 486a and 486b between ridges 485a-485c, help reduce the amount of friction between the elastomeric surface of wiper 460 and inner surface 464 while ridges 485a and 485c maintain a fluid tight seal. In the illustrated embodiment, ridge 485b acts to eliminate the presence of air between ridges 485a and 485c. As seen in the cross section view of FIG. 19A, the inner surface 498 of wiper 460 includes circumferential protrusions 499a and 499b. The pressure of these protrusions against manifold shaft 458 causes formation of ridges 485a and 485c. Ridge 485b is formed by the presence of shim 500 on manifold shaft 458. It will be appreciated that ridge 485b could be configured to create a greater friction force against outer surface 464 by placement of a circumferential protrusion similar to protrusions 499a and 499b.

Referring to FIGS. 19 and 19A, it is believed that the area within valleys 486a and 486b can trap air which, when wiper 460 moves past fluid flow channel 466, could be forced into patient port 433, out patient tubing 418 and ultimately into the patient. The ill effects of air entering the patient's vascular system are well known. Hence, to reduce the chance of air entering the patient, manifold shell 450 can include projections 487a and 487b that substantially fill the valleys 486a and 486b between ridges 485a-485c when manifold wiper 460 is in the low pressure position, i.e., closest to high pressure port 432. As illustrated in FIG. 19A, the interdigitation of ridges 485a-c with protuberances 487a-b reduces dead air space and the air present in valleys 486a-486b thus reducing the chance for air to move into patient port 433 as wiper 460 is moved from the low pressure position.

Figure 20:
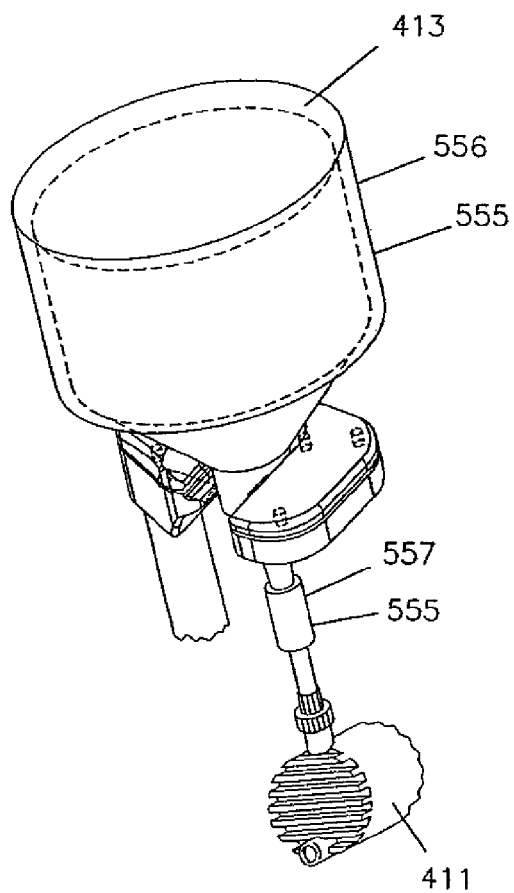
FIG. 20 is a perspective view of two different embodiments for an injection material temperature control device according to the invention.

FIG. 20, illustrates two different embodiments of temperature control device 555 for the fluid in reservoir 413 (22). The temperature control device 555 provides for heating or cooling of the injection material prior to passing into syringe 411. In one embodiment, the temperature control device 555 can be a jacket, 556, that sufficiently covers reservoir bottle 413 to effect the temperature of the material in the reservoir. In an alternative embodiment, the temperature control device can be a tubular heating element or heat exchanger 557 that warms the contrast material as it passes through the tubing 557 before entering syringe 411.

FIGS. 21-25 show a preferred embodiment of a remote control device 550 which includes a main housing 501, which is designed to conform to the user's hand. Trigger 502 is moveable with respect to housing 501, and the position of trigger 502 generates a command signal which is a function of trigger position. The flow rate of contrast material during the patient inject operation is directly proportional to trigger position.

Figure 21:
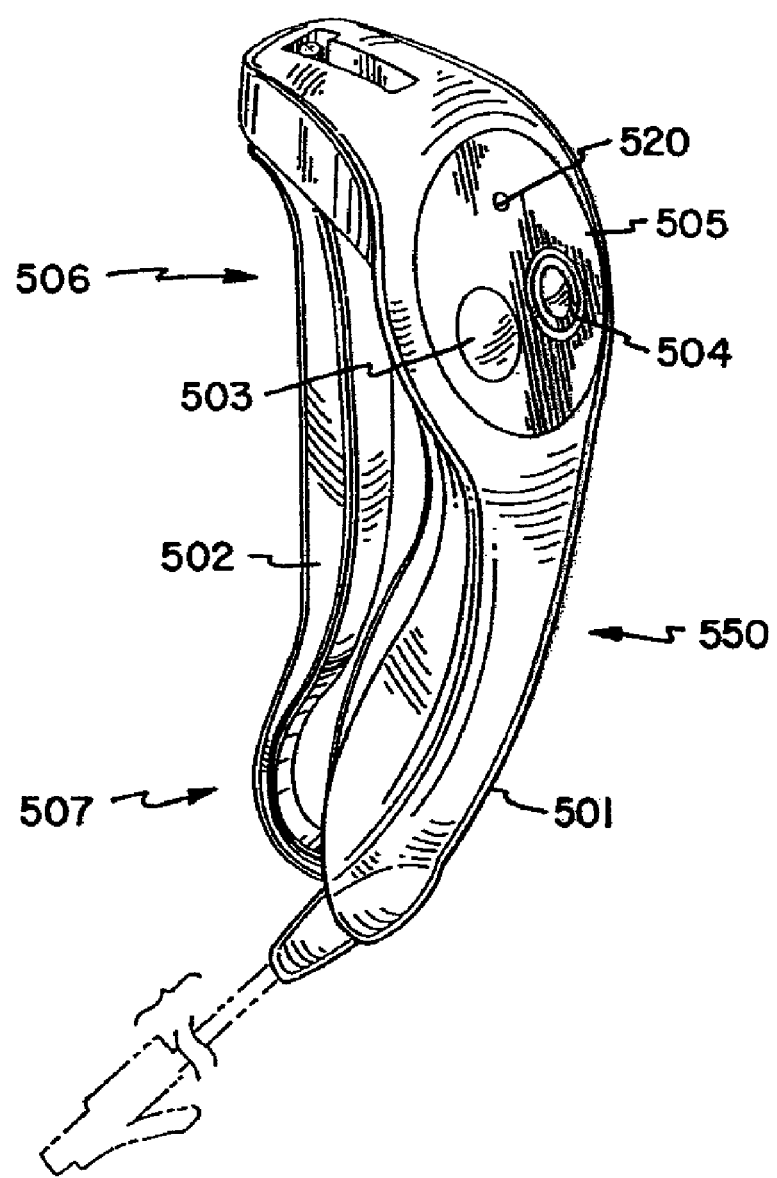
FIG. 21 is a perspective view of embodiment of a remote control according to the invention.

FIG. 21 is a perspective view of remote control 550. In use, remote control 550 is preferably held in the user's hand such that the operation buttons, for example, 503 and 504, on face panel 505, can be readily actuated by the user's thumb. Trigger 502 can be operated by pulling trigger 502 toward housing 501 with one or more of the user's fingers. Referring to the orientation of remote control 550 in the figures, it will be appreciated that there is an upper end 506 and a lower end 507. Referring to the top view of FIG. 25, housing 500 includes a slot 508 that guides the lateral travel of trigger 502 through guide pin 509. Also, as trigger 502 is pulled, the forward and backward travel of trigger 502 is limited. Backwall 510 of slot 508 limits backward travel and forward wall 511 of slot 508 limits forward travel. As illustrated in FIG. 25, slot 508 can be in the form of an "L" 512. The "L" configuration of slot 508 provides for guide pin 509 to rest within the short arm of the L when not in use, and requires lateral movement of trigger 502 to dislodge guide pin 509 from the short arm before trigger 502 can be pulled towards housing 501. This feature of remote control 500 helps prevent against accidental patient injection without an affirmative lateral movement of trigger 502 by the operator.

The bottom end 507 of trigger 502 can mount with housing 501 through a pivot arrangement, for example, a spring hinge or a flexible material which provides for repeated pulling of handle 502 towards housing 501 and return to the forward position when the operator releases trigger 502.

A maximum and minimum fluid discharge rate is set by the operator for the remote control prior to operation. The rate of fluid discharge can be varied by the operator and is directly proportional to the trigger position. That is, in one embodiment, the farther back that trigger 502 is pulled toward housing 501, the greater the fluid discharge rate up to the preset maximum.

Referring to FIGS. 21 and 24, face panel 505 can include an indicator light 520 which illuminates when the system is armed and ready for use. Other control functions can be operated at the face panel. For example, in one embodiment, operation button 504 provides for a saline flush through the low pressure side of the system, and operation button 503 provides a "spritz" function through the high pressure side of the system. It will be appreciated that other functions can be remotely controlled through operation buttons installed at the face panel 505.

As stated above, in one embodiment, face panel 505 includes an operation button 503 providing a "spritz" function. According to this embodiment, activation of operation button 503 will cause injection of a predetermined volume of contrast media at the operator's discretion. This function may be particularly useful when determining position of catheter in a heart, peripheral vessel or other anatomical location in the body. In one embodiment, activation of the spritz button will inject a volume of contrast media that is a percentage of the preset injection volume. For example, activation of a spritz button could inject 10% of the injection during small hunting procedures.

Figure 26:
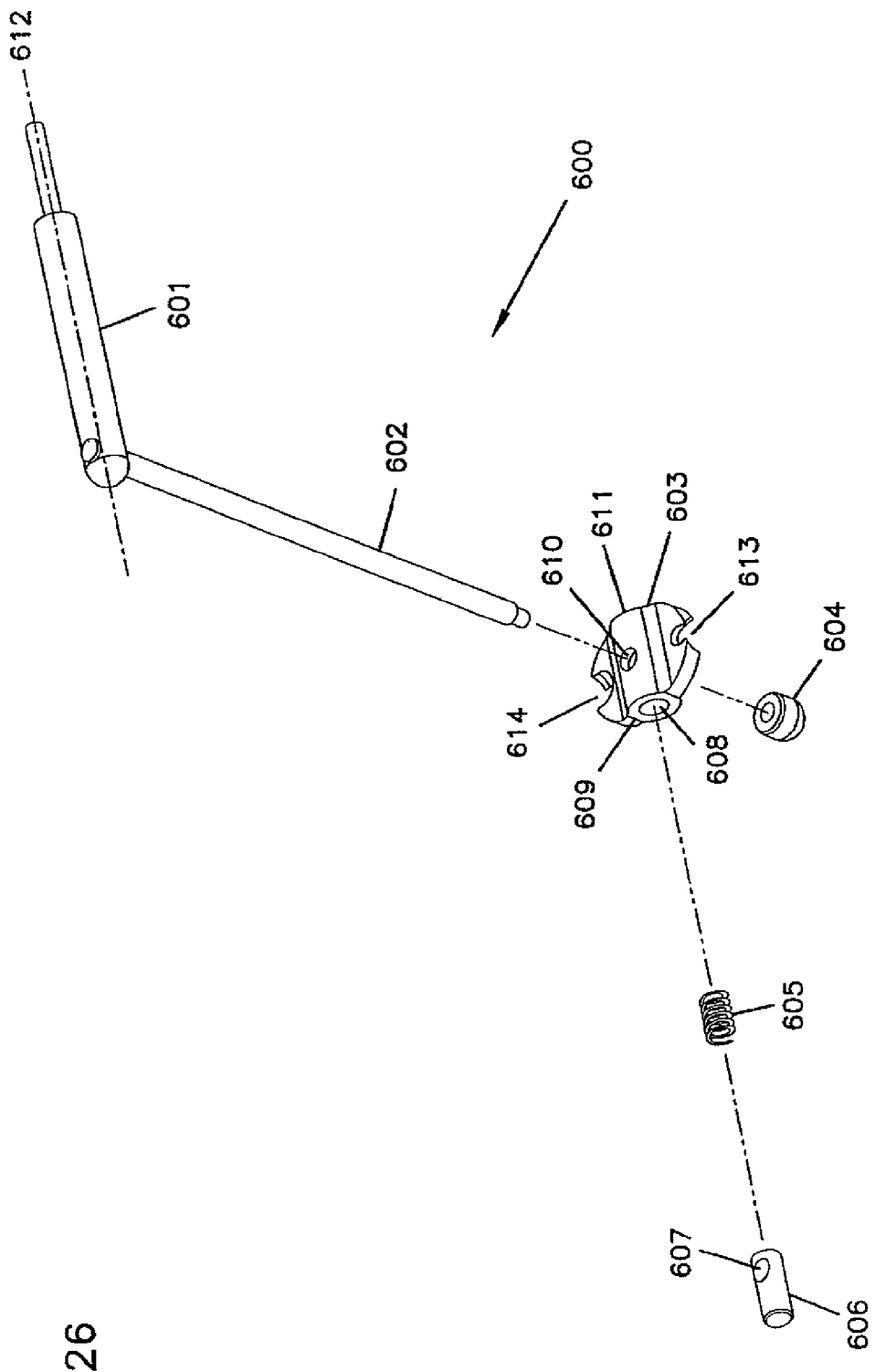
FIG. 26 is an exploded perspective view of an adjustable transducer holder according to the invention.

In some embodiments, an angiographic injector system according to the invention can include a transducer holder 600 for selective positioning of transducer 430 relative to the patient's heart line. As illustrated in FIGS. 9 and 26, transducer holder 600 includes a mounting shaft 601, for mounting transducer holder 600 to console 401, and adjustment shaft 602 for slidable adjustment of transducer 430 in transducer carrier 603. Movement of transducer carrier 603 along adjustment shaft 602 is limited at a first end by mounting shaft 601 and at a second end by adjustment shaft cap 604. Depressing adjustment sleeve 606 allows transducer carrier 603 to be moved freely along adjustment shaft 602.

In the illustrated embodiment, transducer carrier 603 includes two sites, 613 and 614 for mounting transducer 430. These sites are configured to conform to the shape of transducer 430 or transducer dome 438 for a snug fit regardless of the rotational orientation of adjustment shaft 602.

Referring to FIG. 26, spring 605 and adjustment sleeve 606 are located within chamber 608 of carrier 603. Adjustment sleeve 606 includes a channel 607 which fits around adjustment shaft 602. Adjustment shaft 602 also passes through channel 610 of transducer carrier 603. In use, when adjustment sleeve 606 is depressed towards end 611 of transducer carrier 603 such that channel 607 and channel 610 are in axial alignment, transducer carrier 603 can be slidably moved along adjustment shaft 602. Upon release of pressure on adjustment sleeve 606 channel 607 of adjustment sleeve 606 is biased out of axial alignment with channel 610 creating a friction force which holds transducer carrier 603 in position.

In addition to slidable adjustment of carrier 603 along adjustment shaft 602, shaft 602 can be rotated 360° around an axis 612 through mounting shaft 601. Thus, between rotational adjustment and slidable adjustment, transducer 430, mounted in transducer carrier 603, can be positioned at the optimum location for monitoring a patient's blood pressure.

In one preferred embodiment, when the volume of contrast material in syringe 411 is less than the injection volume as determined by the microprocessor, the injector system will prevent subsequent injection operations or automatically refill syringe 411. In auto mode or manual mode, syringe 411 can be refilled maximally or to some lesser volume entered by the operator at console 401. In automatic mode, subsequent to completion of an injection, computer 100 compares the volume of contrast material remaining in syringe 411 with the injection volume preset in the computer by the operator. If the preset injection volume is greater than the volume of contrast material available in syringe 411, computer 100 prevents subsequent patient injection operations. Provided contrast reservoir 413 (or 22) is in place, computer 100 can energize the motor drive circuitry to automatically retract plunger 412 at a set rate, preferably corresponding to a flow rate of about 3 ml per second, to load syringe 411 with contrast material to maximum or other preset volume. Once syringe 411 is filled as indicated by the reverse limit feedback signal from sensor 164, motor 104 moves plunger 412 forward to purge air from the syringe out one-way valve 414 at a rate of about 3 ml per second.

It has also been discovered that by using multiple speeds for retracting of plunger 412 during syringe refill, an air forming bubble within syringe 411 can be reduced more readily. For example, assume a situation where syringe 411 is to be maximally filled. According to this example, the computer controlled retraction of plunger 412 occurs slowly at a rate of about 2 ml per second until filled with about 40 ml of media. This slower rate facilitates a forming air bubble to break free from the surface of plunger 412 at the meniscus. Subsequently, a faster rate of about 3 ml per second is used to complete the filling procedure and the bubble released from plunger 412 will tend to float away from the plunger toward one-way valve 414. In addition, angulation of syringe 411 at about 10-20°, preferably about 15° from horizontal facilitates release or movement of an air bubble to one-way valve 14.

In conclusion, the injector system of the present invention provides interactive control of the delivery of radiographic contrast material to a catheter through a user actuated proportional control. The several embodiments disclosed herein enhance the safety and efficiency of the injector system as well as providing for the user to adjust the parameters for injection of contrast material interactively as needed and as the patient's condition changes.

Although the present invention has been described with reference to preferred embodiments, workers skilled in the art will recognize that changes may be made in form and detail without departing from the spirit and scope of the invention. For example, syringe holder 16 and 410 may take other forms, such as an end loaded cylinder. Similarly, manifolds 26 and 417 can take other configurations and can incorporate, for example, a part of syringe ports 78 and 80.

What is claimed is:

1. A powered injector for injecting a fluid into a patient in conjunction with a medical imaging procedure, the powered injector comprising:
   a plunger drive ram,
   a motor for moving the plunger drive ram,
   a syringe holder configured to couple a syringe to the powered injector to permit the plunger drive ram to engage and move a plunger within the syringe;
   a fluid reservoir adapted to be in fluid communication with a chamber of the syringe;
   a control circuit configured to control the motor to advance the plunger drive ram to inject fluid from the chamber of the syringe, and to retract the plunger drive ram to draw fluid from the fluid reservoir into the chamber of the syringe,
   said powered injector configured to:
      advance the plunger drive ram to perform a first injection of fluid from the chamber of the syringe;
      determine an amount of fluid remaining in the chamber of the syringe following the first injection;
      receive a user input associated with a second injection via the powered injector, the user input comprising a safety parameter for the subsequent injection selected from the group consisting of maximum injection volume, maximum flow rate, maximum pressure, and rise time;
      determine an amount of fluid to be delivered via the powered injector during the second injection based on the user input received;
      compare the amount of fluid remaining in the chamber of the syringe with the amount of fluid to be delivered during the second injection; and either
      (a) advance the plunger drive ram to perform the second injection if the amount of fluid to be delivered is equal to or less than the amount of fluid remaining in the chamber of the syringe, or
      (b) retract the plunger drive ram to draw fluid from the fluid reservoir into the chamber of the syringe if the amount of fluid to be delivered is greater than the amount of fluid remaining in the chamber.

2. The powered injector of claim 1 wherein the plunger drive ram is retracted to a predetermined position to draw fluid from the fluid reservoir into the chamber of the syringe if the amount of fluid to be delivered is greater than the amount of fluid remaining in the chamber.

3. The powered injector of claim 2 wherein retracting the plunger drive ram to the predetermined position maximally fills the chamber of the syringe.

4. The powered injector of claim 2 wherein retracting the plunger drive ram to the predetermined position draws an amount of fluid into the chamber that partially fills the chamber of the syringe.

5. The powered injector of claim 1 wherein, after retracting the plunger drive ram to draw fluid from the fluid reservoir into the chamber of the syringe, the powered injector is further configured to advance the plunger drive ram to purge air from the chamber of the syringe.

6. The powered injector of claim 1 wherein the user input comprises a maximum injection volume for the second injection.

7. The powered injector of claim 1 wherein the powered injector is further configured to retract the plunger drive ram at a first speed followed by a second speed, the first speed being slower than the second speed.

8. The powered injector of claim 7 wherein the first speed is about 2 mL/sec.

9. The powered injector of claim 7 wherein the second speed is about 3 mL/sec.

10. The powered injector of claim 7 wherein the powered injector is further configured to retract the plunger drive ram at the first speed until a predetermined volume of fluid has been drawn into the chamber.

11. The powered injector of claim 7 wherein the plunger drive ram is retracted at a rate of about 2 mL/sec until about 40 mL of fluid have been drawn into the chamber, and wherein the plunger drive ram is retracted at a rate of about 3 mL/sec thereafter.

* * * * *